(12) United States Patent
Jorgensen et al.

(10) Patent No.: US 8,129,530 B2
(45) Date of Patent: Mar. 6, 2012

(54) CATECHOLAMINE DERIVATIVES AND PRODRUGS THEREOF

(75) Inventors: Morten Jorgensen, Bagsvaerd (DK); Benny Bang-Andersen, Copenhagen S (DK); Ask Puschl, Frederiksberg (DK); Niels Mork, Virum (DK); Jennifer Larsen, Roskilde (DK)

(73) Assignee: H. Lundbeck A/S, Valby (DK)

( * ) Notice: Subject to any disclaimer, the term of this patent is extended or adjusted under 35 U.S.C. 154(b) by 820 days.

(21) Appl. No.: 12/193,979

(22) Filed: Aug. 19, 2008

(65) Prior Publication Data

US 2009/0062324 A1 Mar. 5, 2009

Related U.S. Application Data

(60) Provisional application No. 60/969,299, filed on Aug. 31, 2007.

(51) Int. Cl.
*A61K 31/4353* (2006.01)
*C07D 487/00* (2006.01)
(52) U.S. Cl. .......................................... 546/65; 514/285
(58) Field of Classification Search .................... 546/65; 514/285
See application file for complete search history.

(56) References Cited

U.S. PATENT DOCUMENTS

2009/0124651 A1   5/2009   Jorgensen et al.
2009/0325942 A1   12/2009  Keil

FOREIGN PATENT DOCUMENTS

| CH | 648300 | 3/1985 |
|---|---|---|
| WO | WO 97/17326 | 5/1997 |
| WO | WO-0214279 | 2/2002 |
| WO | WO-02100377 | 12/2002 |
| WO | WO 2008/092872 | 8/2008 |
| WO | WO 2009/027482 | 3/2009 |
| WO | WO 2009/027746 | 3/2009 |
| WO | WO 01/78713 | 10/2010 |

OTHER PUBLICATIONS

Tamminga et al., Trans., 109(3), 411 (2002).
F. Bibbiani, L.C. Constantini, R patel, T.N. Chase Experimental Neurology 2005, 192, 73.
Baldessarini, Ram, Neumeyer; Neuroropharmacology, 21 (10), 953 (1982).
Journal of Pharmaceutical Science, 66, 2-19 (1977).
Lin, Haadsma-Svensson, Phillips, Lahti, McCall, Piercey, Schreur, von Voigtlander, Smith, Chidester; J. Med. Chem., 36(8), 1069 (1993).
Taber, Neubert, Rheingold; J. Am. Chem. Soc., 124(42), 12416 (2002).
Mellin, Hacksell; Tetrahedron, 23(22), 5443 (1987).
Gemsler, Samour; J. Org. Chem., 18(1), 9, (1953).
Cabiddu, Cadoni, De Montis, Fattuoni, Melis, Usai; Tetrahedron, 59(24), 4383, (2003).
Ram, Neumeyer, J. Org. Chem., 46(13), 2830 (1981).
Nichols, Brewster, Johnson, Oberlender, Riggs; J. Med. Chem., 33(2), 703 (1990).
Bourry, Akue-Gedu, Rigo, Henichart, Sanz, Couturier; J. Heterocycl. Chem., 40, 989 (2003).
Ungerstedt, Arbuthnot; Brain Res., 24, 485 (1970).
Setler, Sarau, Zirkle, Sauders; J. Pharmacol., 50(4), 419 (1978).
Ungerstedt, Herrera-Marschitz, Jungnelius, Stahle, Tossman, Zetterstrom "Advances in Dopamine Research" (Kohsaka Ed.), Pergamon Press, Oxford, p. 219 ( 1982).
Arnt, Hytell; Psychopharmacology, 85(3), 346 (1985).
Sonsalla, Manzino, Heikkila; J. Pharmacol Exp. Ther., 247(1), 189 (1988).
Lundblad, Adndersson, Winkler, Kirik, Wierup, Cenci; Eur. J. Neurosci., 15(1), 120 (2002).
Liu, et al., J. Med. Chem., 2006, 49 (4), 1494-1498.
Liu, Ph.D. thesis. University of Groningen 2006.
Liu et al: "A novel synthesis and pharmacological evaluation of a potential dopamine D1/D2 agonist: 1-Propyl-1, 2, 3, 5, 4a, 5, 10, 10a-octahydrobenz o[g ] quinoline-6, 7-diol" Bioorganic & Medicinal Chemistry, Elsevier Science Ltd, GB, vol. 16, No. 6, Jun. 23, 2007, pp. 3438-3444, XP022558577 ISSN: 0968-0896 paragraph [0001]; table 1; compound 4.

*Primary Examiner* — Rita Desai
(74) *Attorney, Agent, or Firm* — H. Lundbeck A/S

(57) ABSTRACT

The present invention relates to novel catecholamine derivatives of Formula I, to processes for their preparation, pharmaceutical compositions containing them and to their use in therapy.

12 Claims, 2 Drawing Sheets

Figure 1:
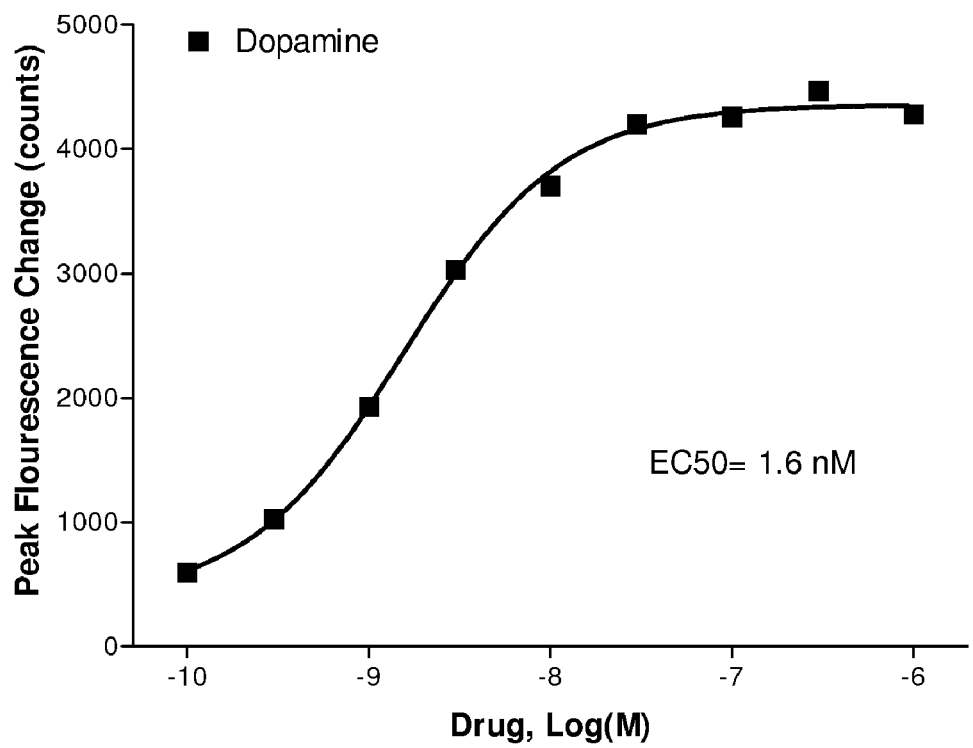

Dose-response curve for dopamine.

Crystal structure of example 2d2. The absolute configuration was determined by the anomalous scattering of the 'heavy' bromine atom.

CATECHOLAMINE DERIVATIVES AND PRODRUGS THEREOF

This application claims the benefit of priority under 35 U.S.C. §119(e) of provisional application 60/969,299, filed Aug. 31, 2007, which is hereby incorporated by reference in its entirety.

FIELD OF THE INVENTION

The present invention relates to novel catecholamines and catecholamine derivatives, to processes for their preparation, pharmaceutical compositions containing them and their use in therapy. Further, the compounds of the invention may be useful as PET ligands.

BACKGROUND ART

Neurodegenerative diseases such as Alzheimer's and Huntington's disease are becoming more prevalent with the aging population. One particular neurodegenerative disease, which typically has its onset between the ages of 50 and 80 years of age, is Parkinson's disease (PD). PD is a disorder of the brain, which is characterized by tremor and difficulty with walking, movement, and coordination.

Dopamine (DA) is a chemical neurotransmitter, which is utilized by brain cells to transmit impulses to control or modulate peripheral muscle movement. PD is believed to be caused by a progressive deterioration of DA-containing neurons in the substantia nigra zona compacta of the brain. The degeneration of the DA-containing neurons results in reduced amounts of DA in the brain. This process is thought to disturb the nerve cell function such that impulses are not transmitted properly, resulting in a loss of muscle control and function.

Currently, there is no cure for PD. Treatments are typically aimed at controlling the PD symptoms, primarily by replacing the DA with either (levo)-3,4-dihydroxy phenylalanine (L-DOPA) which is metabolized to DA, or by administering chemical agents that stimulate the DA receptors. These receptors fall into two broad classes, D1-type and D2-type receptors. The former is divided into D1 and D5 receptors, while the D2 receptor family consists of D2, D3, and D4 receptors.

Certain hydroxylated (phenols or catechols) phenylethylamines (as such or forming part of a semirigid/rigid ring system) are known to possess dopaminergic activity at least in animal models. However, their clinical use is limited because they have low or no oral bioavailability, most likely due to their high first-pass metabolism. However, Apomorphine, which belongs to this class of compounds, is used clinically in PD therapy albeit with a non-oral delivery (typically intermittent subcutaneous administration or daytime continuous infusion). Several clinical studies are ongoing with alternative delivery strategies for Apomorphine therapy in PD such as intranasal and sublingual formulations. However these efforts are yet to result in an option for the clinical treatment of PD.

Direct DA receptor agonists are able to activate the DA autoreceptors as well as the postsynaptic DA receptors. The effects of autoreceptor stimulation appear to predominate when e.g. Apomorphine is administered at low doses, whereas at higher doses the attenuation of DA transmission is outweighed by the enhancement of postsynaptic receptor stimulation. The antipsychotic effects in man of low doses of e.g. Apomorphine are likely due to the autoreceptor stimulation [for a discussion of clinical data, see: Tamminga; J. Neurol. Trans., 109(3), 411 (2002)].

L-DOPA is an efficacious PD drug (a prodrug of dopamine) with a poor PK profile leading to dyskinesia and other response fluctuations. Selective D2-agonists (e.g. Pramipexole) give less dyskinesia, but lack efficacy in late PD and eventually need complementation or replacement with L-DOPA. L-DOPA and Apomorphine are currently the most efficacious PD drugs and they stimulate both D1 and D2 receptors.

As mentioned previously, the poor oral bioavailability of catecholamines has prevented their clinical use as oral drugs. The related phenolic amines have similar poor oral bioavailability limiting their clinical use as orally active drugs. However, Rotigotine, which belongs to this class of compounds, was recently introduced as a new PD drug based on a transdermal delivery. For Apomorphine, animal studies have shown that transdermal delivery or via implants may provide possible forms of administration. However, when the delivery of Apomorphine from implants was studied in monkeys [F. Bibbiani, L. C. Constantini, R. Patel, T. N. Chase Experimental Neurology 2005, 192, 73] it was found that in most cases the animals had to be treated with the immunosuppressant Dexamethasone to prevent local irritation and other complications following the implantation surgery. Transdermal delivery of Apomorphine has also been associated with local skin irritation and coloration.

Apart from PD, other diseases in which an increase in dopaminergic turnover may be beneficial are geriatrics, for preventing bradykinesia and depression and in the improvement of mental functions including various aspects of cognition as discussed above. It can have a positive effect in depressed patients, and it can be used in obesity as an anorectic agent. It can improve minimal brain dysfunction (MBD), narcolepsy, and potentially the negative, the positive as well as the cognitive symptoms of schizophrenia. Restless leg syndrome (RLS) and periodic limb movement disorder (PLMD) are alternative indications, which are clinically treated with DA-agonists. In addition, impotence and erectile dysfunction are also likely to be improved by treatment with DA-agonists. Thus, improvement of sexual functions in both women and men is another possible indication for treatment with DA-agonists since erectile dysfunction (impotence in men) and sexual stimulation in e.g. menopausal women (stimulation of vaginal lubrication and erection of clitoris) potentially can be achieved via DA-receptor stimulation. In this context, it is noteworthy that Apomorphine when given sublingually is used clinically to improve erectile dysfunction. Clinical studies of L-DOPA and the D2 agonist Pramipexole therapy in Huntington's disease have shown promising results; thus treatment of Huntington's disease is another potential application of the compounds of the invention. DA is involved in regulation of the cardiovascular and renal systems, and accordingly, renal failure and hypertension can be considered alternative indications for the compounds of the invention.

An alternative to the non-oral formulations of the catecholamines involves the use of a prodrug. A problem associated with the development of such compounds for clinical use is the difficulties associated with predicting conversion to the catecholamine itself in humans. Various ester prodrugs of catecholamines have been reported in the literature such as enterically coated NPA esters for duodenal delivery [see eg. Wikström, Dijkstra, Cremers, Ivo; WO 02100377], and the D1-like agonist Adrogolide [ABT-431; DAS-431, a diacetyl prodrug of A-86929]. Adrogolide undergoes a high hepatic first-pass metabolism in man after oral dosing and, as a result, has a low oral bioavailability (app. 4%). In PD patients, intravenous (IV) Adrogolide has antiparkinson efficacy comparable to that of L-DOPA [Giardina, Williams; CNS Drug Reviews, 7, 305 (2001)]. An alternative approach involves the 'masking' of the two hydroxyl groups in the catechol as the corresponding methylene-di-oxy (MDO) acetal, as the acetal derived from other aldehydes than formaldehyde, or as the ketal derived from various ketones. This prodrug principle has been reported for the Aporphines more than 20 years ago [Baldessarini, Ram, Neumeyer; Neuroropharmacology, 21(10), 953 (1982)]. Of these potential prodrugs to Apomorphine and related compounds, only that derived from N-n-propyl Apomorphine (NPA) and formaldehyde showed significant efficacy in animal models of PD. Over the following ~25 years, these findings have not lead to a PD drug based on the MDO-masked Apoporphines or related compounds.

Despite the long-standing interest in the field, there is evidently still an unmet need as regards developing efficient, well-tolerated and orally active drugs for the treatment of PD. A mixed D1-like/D2-like agonist giving continuous dopaminergic stimulation may fulfill such unmet needs.

SUMMARY OF THE INVENTION

The present invention relates to novel catecholamine derivatives, which the inventors have found may offer suitable alternatives to current marketed treatments of neurodegenerative diseases such as PD and Huntington's disease and to the treatment of other indications discussed herein, such as eg. dyskinetic disorders, cognitive impairment and restless legs syndrome (RLS), and to compounds that are in vivo metabolizable prodrugs hereof.

Cognitive impairment can be experienced in several patients groups, e.g. schizophrenic, depressive or psychotic patients and patients with attention deficit hyperactivity disorder (ADHD), Parkinson's disease, mild cognitive impairment (MCI), dementia, anxiety, age associated memory impairment, Alzheimer's Disease or post-traumatic stress disorder and patients taking benzodiazepines or tricyclic anti-depressants and in a range of neurodegenerative diseases in addition to Parkinson's Disease and Alzheimer's Disease. The phrase "cognitive impairment" refers to the difficulties with attention, learning, memory and executive function (relevant reactions to external stimuli). These can include: deficits in attention, disorganized thinking, slow thinking, difficulty in understanding, poor concentration, impairment of problem solving, poor memory, difficulty in expressing thoughts and/or difficulty in integrating thoughts, feelings and behaviour and extinction of irrelevant thoughts as well as attention and vigilance, verbal learning and memory, visual learning and memory, speed of processing and social cognition.

The objective of the present invention is to provide novel compounds, which are both potent dopamine D1-like and D2-like agonists, and which may be used in the treatment of neurological and psychiatric diseases A further objective of the present invention is to provide novel compounds for oral administration in the treatment of PD and other diseases or disorders, which responds favourably to an increased dopaminergic turnover.

PET (positron emission tomography) analysis is an important tool in the diagnosis of PD. Some of the compounds of the invention have potential applications as PET ligands for imaging studies of the DA-receptors or as intermediates for the preparation of such ligands, which may, for example, be applied in receptor localization studies as well as for the determination of receptor occupancy determination for compounds with affinities for the DA receptors. A further objective is therefore to provide radiolabeled compounds of the present invention, which are considered to be valuable PET ligands.

Further objectives of the invention will become apparent upon reading the present specification.

Accordingly, in one aspect the present invention relates to compounds of formula I:

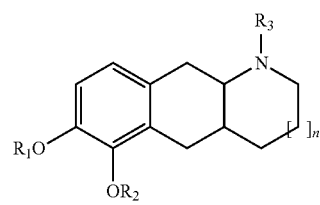

wherein n=0, 1

R$_1$ and R$_2$ are independently selected from hydrogen, C$_{1-6}$ alkanoyl, phenylacetyl or benzoyl, or wherein R$_1$ and R$_2$ are fused and form a methylene (CH$_2$) group, a carbonyl (C=O) group, or an oxalyl (O=C—C=O) group R$_3$ is selected from the group consisting of hydrogen, methyl, ethyl, n-propyl, cyclo-propyl, cyclo-butyl, allyl, propargyl, hydroxyethyl, 3-fluoropropyl and 2-fluoroethyl and addition salts thereof with pharmaceutically acceptable acids, provided that the compound is not one of the following racemates:

Racemic-1,2,3,4,4a,5,10,10a-octahydro-benzo[g]quinoline-6,7-diol

Racemic-1-methyl-1,2,3,4,4a,5,10,10a-octahydro-benzo[g]quinoline-6,7-diol

Racemic-1-ethyl-1,2,3,4,4a,5,10,10a-octahydro-benzo[g]quinoline-6,7-diol

Racemic-1-n-propyl-1,2,3,4,4a,5,10,10a-octahydro-benzo[g]quinoline-6,7-diol

The C$_{1-6}$ alkanoyl group means a straight-chain or branched-chain alkanoyl group containing from 1 to six carbon atoms, examples of which include a formyl group, an acetyl group, a pivaloyl group, and the like.

In a particular embodiment, the invention relates to compounds of formula I in the form of a substantially pure single enantiomer or a single diastereomer.

In another particular embodiment, the invention relates to compounds of formula I in the form of a mixture of enantiomers, a mixture of diastereomers, or a substantially pure polymorph.

In a particular embodiment, the invention relates to compounds of Formula I which have trans-fused ring systems. In another embodiment the invention relates to compounds of Formula I, which have cis-fused ring systems.

In an embodiment the invention relates to compounds of Formula I, for which n=0. In another embodiment the invention relates to compounds of Formula I, for which n=1.

In separate embodiments of the invention, the compound is selected from one of the specific compounds disclosed in the Experimental Section.

In a particular embodiment, the invention relates to compounds of Formula I wherein R$_3$ is selected from the group consisting of hydrogen, methyl, ethyl, n-propyl, allyl, and propargyl. In another embodiment, the invention relates to compounds of Formula I wherein R$_3$ is selected from the group consisting of cyclo-propyl, cyclo-butyl, and hydroxyethyl.

In a specific embodiment, the invention relates to compounds of Formula I wherein n=1, and which are further characterized by being the substantially pure (4aR,10aR)-enantiomer.

The invention furthermore relates to compounds of Formula I wherein $R_1$ and $R_2$ are both hydrogen and $R_3$ is selected from the group consisting of hydrogen, methyl, ethyl and n-propyl. The invention also relates to compounds of Formula I wherein $R_1$ and $R_2$ are fused and form a methylene ($CH_2$) group, and $R_3$ is selected from the group consisting of hydrogen, methyl, ethyl and n-propyl, such as methyl and n-propyl.

In separate embodiments of the invention, the compound is selected from one of the following specific compounds:

trans-1-methyl-2,3,3a,4,9,9a-hexahydro-1H-benzo[f]indole-5,6-diol
cis-1-methyl-2,3,3a,4,9,9a-hexahydro-1H-benzo[f]indole-5,6-diol
trans-1-n-propyl-2,3,3a,4,9,9a-hexahydro-1H-benzo[f]indole-5,6-diol
cis-1-n-propyl-2,3,3a,4,9,9a-hexahydro-1H-benzo[f]indole-5,6-diol
(4aR,10aR)-1,2,3,4,4a,5,10,10a-octahydro-benzo[g]quinoline-6,7-diol
(4aS,10aS)-1,2,3,4,4a,5,10,10a-octahydro-benzo[g]quinoline-6,7-diol
(4aR,10aR)-1-methyl-1,2,3,4,4a,5,10,10a-octahydro-benzo[g]quinoline-6,7-diol
(4aS,10aS)-1-methyl-1,2,3,4,4a,5,10,10a-octahydro-benzo[g]quinoline-6,7-diol
(4aR,10aR)-1-ethyl-1,2,3,4,4a,5,10,10a-octahydro-benzo[g]quinoline-6,7-diol
(4aS,10aS)-1-ethyl-1,2,3,4,4a,5,10,10a-octahydro-benzo[g]quinoline-6,7-diol
(4aR,10aR)-1-n-propyl-1,2,3,4,4a,5,10,10a-octahydro-benzo[g]quinoline-6,7-diol
(4aS,10aS)-1-n-propyl-1,2,3,4,4a,5,10,10a-octahydro-benzo[g]quinoline-6,7-diol
(4aR,10aR)-1-(2-hydroxyethyl)-1,2,3,4,4a,5,10,10a-octahydro-benzo[g]quinoline-6,7-diol
(4aR,10aR)-1-allyl-1,2,3,4,4a,5,10,10a-octahydro-benzo[g]quinoline-6,7-diol
(4aR,10aR)-1-prop-2-ynyl-1,2,3,4,4a,5,10,10a-octahydro-benzo[g]quinoline-6,7-diol
(4aR,10aR)-1-cyclo-propyl-1,2,3,4,4a,5,10,10a-octahydro-benzo[g]quinoline-6,7-diol
(4aR,10aR)-1-cyclo-butyl-1,2,3,4,4a,5,10,10a-octahydro-benzo[g]quinoline-6,7-diol
(6aR,10aR)-6,6a,7,8,9,10,10a,11-octahydro-1,3-dioxa-7-aza-cyclopenta[a]anthracene
(6aR,10aR)-7-methyl-6,6a,7,8,9,10,10a,11-octahydro-1,3-dioxa-7-azacyclopenta[a]anthracene
(6aR,10aR)-7-ethyl-6,6a,7,8,9,10,10a,11-octahydro-1,3-dioxa-7-aza-cyclopenta[a]anthracene
(6aR,10aR)-7-n-propyl-6,6a,7,8,9,10,10a,11-octahydro-1,3-dioxa-7-aza-cyclopenta[a]anthracene
Acetic acid (4aR,10aR)-7-acetoxy-1,2,3,4,4a,5,10,10a-octahydro-benzo[g]quinolin-6-yl ester
Acetic acid (4aS,10aS)-7-acetoxy-1,2,3,4,4a,5,10,10a-octahydro-benzo[g]quinolin-6-yl ester
2,2-Dimethylpropionic acid (4aR,10aR)-7-(2,2-dimethyl-propionyloxy)-1-methyl-1,2,3,4,4a,5,10,10a-octahydro-benzo[g]quinolin-6-yl ester
Acetic acid (4aS,10aS)-6-acetoxy-1-methyl-1,2,3,4,4a,5,10,10a-octahydro-benzo[g]quinolin-7-yl ester
Acetic acid (4aS,10aS)-6-acetoxy-1-ethyl-1,2,3,4,4a,5,10,10a-octahydro-benzo[g]quinolin-7-yl ester
2,2-Dimethylpropionic acid (4aR,10aR)-7-(2,2-dimethyl-propionyloxy)-1-n-propyl-1,2,3,4,4a,5,10,10a-octahydro-benzo[g]quinolin-6-yl ester
or a pharmaceutically acceptable acid addition salt thereof In another aspect the present invention relates to radiolabeled compounds of Formula I and the use thereof in various biological assays such as PET-studies, in vivo binding studies and in vitro assays.

In a further aspect the invention provides the use of a compound of Formula I, or a pharmaceutically acceptable acid addition salt hereof, as a medicament.

The compound of Formula I, either as the free base, or as a pharmaceutically acceptable acid addition salt, or as a pharmaceutical composition, may be administered in any suitable way e.g. orally, buccally, sublingually, non-orally or parenterally, and the compound may be presented in any suitable form for such administration, e.g. orally in the form of tablets, capsules, powders, syrups, solutions or dispersions, non-orally in the form of eg. transdermal patches or parenterally in the form of dispersions or solutions for injection. In one embodiment, the compound of Formula I is administered in the form of a solid pharmaceutical entity, suitably as a tablet or a capsule.

The compounds of Formula I form pharmaceutically acceptable acid addition salts with a wide variety of organic and inorganic acids. Such salts are also part of this invention.

A pharmaceutically acceptable acid addition salt of the compound of Formula I is formed from a pharmaceutically acceptable acid as is well known in the art. Such salts include the pharmaceutically acceptable salts listed in Journal of Pharmaceutical Science, 66, 2-19 (1977) and are known to the skilled person. Typical inorganic acids used to form such salts include hydrochloric, hydrobromic, hydriodic, nitric, sulphuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include the chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

Methods for the preparation of solid pharmaceutical preparations are also well known in the art. Tablets may thus be prepared by mixing the active ingredient with ordinary adjuvants, fillers and diluents and subsequently compressing the mixture in a convenient tabletting machine. Examples of adjuvants, fillers and diluents comprise microcrystalline cellulose, corn starch, potato starch, lactose, mannitol, sorbitol talcum, magnesium stearate, gelatine, lactose, gums, and the like. Any other adjuvant or additive such as colourings, aroma, preservatives, etc. may also be used provided that they are compatible with the active ingredients.

In particular, the tablet formulations according to the invention may be prepared by direct compression of a compound of Formula I in admixture with conventional adjuvants or diluents. Alternatively, a wet granulate or a melt granulate of a compound of Formula I, optionally in admixture with conventional adjuvants or diluents may be used for compression of tablets.

Solutions of a compound of Formula I for injections may be prepared by dissolving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, solubilising agents, etc. Alternatively the active ingredient, eg. as the free base may be dissolved in a digestible or non-digestible oil, mixtures hereof or similar, to prepare an intramuscular depot formulation capable of releasing the active ingredient over a prolonged period of time.

Pharmaceutical formulations of the compound of Formula I to be used in transdermal applications, such as transdermal patches, may optionally contain permeation activators to facilitate the passage of the active ingredient through the skin.

In another aspect, the invention relates to a pharmaceutical composition comprising a therapeutically effective amount of a compound of Formula I, or a pharmaceutically acceptable acid addition salt thereof, and one or more pharmaceutically acceptable carriers, diluents and excipients.

In a specific embodiment of the invention there is provided a pharmaceutical composition comprising a therapeutically effective amount of a compound of Formula I, or a pharmaceutically acceptable acid addition salt thereof, wherein $R_1$ and $R_2$ are both hydrogen and $R_3$ is selected from the group consisting of hydrogen, methyl, ethyl and n-propyl for non-oral administration, such as transdermal, nasal, buccal, intramuscular or subcutaneous administration.

In a further aspect the invention provides the use of a compound of Formula I or a pharmaceutically acceptable acid addition salt thereof for the preparation of a medicament for the treatment of neurodegenerative disorders such as Parkinson's disease and Huntington's disease.

In a further aspect the invention provides the use of a compound of Formula I or a pharmaceutically acceptable acid addition salt thereof for the preparation of a medicament for the treatment of psychoses, impotence, renal failure, heart failure or hypertension.

In another aspect the invention provides the use of a compound of Formula I, or a pharmaceutically acceptable acid addition salt thereof, for the manufacture of a medicament for the treatment of cognitive impairment in a mammal.

In a still further aspect the invention provides the use of a compound of Formula I, or a pharmaceutically acceptable acid addition salt thereof, for the manufacture of a medicament for the treatment of restless legs syndrome (RLS) or periodic limb movement disorder (PLMD).

In a different aspect the invention provides the use of a compound of Formula I, or a pharmaceutically acceptable acid addition salt thereof, for the manufacture of a medicament for the treatment of movement disorders, poverty of movement, dyskinetic disorders, gait disorders or intention tremor in a mammal.

In a further aspect the invention provides the use of a compound of Formula I or a pharmaceutically acceptable acid addition salt thereof for the treatment of neurodegenerative disorders such as Parkinson's disease and Huntington's disease.

In a further aspect the invention provides the use of a compound of Formula I or a pharmaceutically acceptable acid addition salt thereof for the treatment of psychoses, impotence, renal failure, heart failure or hypertension.

In another aspect the invention provides the use of a compound of Formula I, or a pharmaceutically acceptable acid addition salt thereof, for the treatment of cognitive impairment in a mammal.

In a still further aspect the invention provides the use of a compound of Formula I, or a pharmaceutically acceptable acid addition salt thereof, for the treatment of restless legs syndrome (RLS) or periodic limb movement disorder (PLMD).

In a different aspect the invention provides the use of a compound of Formula I, or a pharmaceutically acceptable acid addition salt thereof, for the treatment of movement disorders, poverty of movement, dyskinetic disorders, gait disorders or intention tremor in a mammal.

In separate aspects the invention provides the use of a compound of Formula I, or a pharmaceutically acceptable acid addition salt thereof, for the manufacture of medicaments, which are intended for oral administration, or for non-oral administration.

The invention also provides a method of treating a mammal suffering from a neurodegenerative disorder such as Parkinson's disease and Huntington's disease comprising administering to the mammal a therapeutically effective amount of a compound of Formula I, or a pharmaceutically acceptable acid addition salt thereof.

In another aspect the invention also provides a method of treating a mammal suffering from psychoses, impotence, renal failure, heart failure or hypertension, comprising administering to the mammal a therapeutically effective amount of a compound of a compound of Formula I, or a pharmaceutically acceptable acid addition salt thereof.

In a further aspect the invention provides a method of treating a mammal suffering from a cognitive impairment, comprising administering to the mammal an effective amount of a compound of Formula I, or a pharmaceutically acceptable acid addition salt thereof.

The invention also relates to a method of treating a mammal suffering from restless legs syndrome (RLS) or periodic limb movement disorder (PLMD), comprising administering to the mammal a therapeutically effective amount of a compound of Formula I, or a pharmaceutically acceptable addition salt thereof.

The invention also relates in a separate aspect to a method of treating a mammal suffering from movement disorders, poverty of movement, dyskinetic disorders, gait disorders or intention tremor comprising administering to the mammal a therapeutically effective amount of a compound of Formula I, or a pharmaceutically acceptable acid addition salt thereof.

In a specific embodiment of the invention the mammal is a human subject

The therapeutically effective amount of a compound of Formula I, calculated as the daily dose of the compound of Formula (I) above as the free base, is suitably between 0.01 and 125 mg/day, more suitable between 0.05 and 100 mg/day, e.g. preferably between 0.1 and 50 mg/day.

In a specific embodiment the daily dose of the compound of Formula I is between 1 and 10 mg/day.

In another embodiment the daily dose of the compound of Formula I is less than about 1 mg/day.

In a separate embodiment the daily dose of the compound of Formula I is about 0.1 mg/day.

In a further embodiment the invention provides an oral formulation comprising from 0.001 mg to 125 mg of a compound of Formula I.

In a further embodiment the invention provides an oral formulation comprising from 0.001 mg to 0.1 mg of a compound of Formula I.

In a further embodiment the invention provides an oral formulation comprising from 0.01 mg to 1 mg of a compound of Formula I.

In a further embodiment the invention provides an oral formulation comprising from 0.1 mg to 10 mg of a compound of Formula I.

FIGURES

FIG. 1: Dose-response curve for the concentration-dependent stimulation of intracellular $Ca^{2+}$ release by dopamine in hD5-transfected CHO-Ga16 cells.

Figure 2:
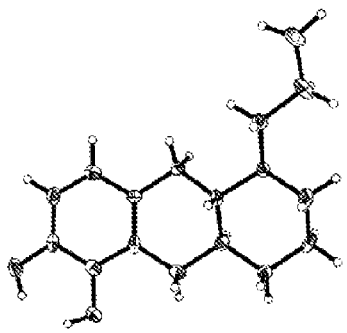

FIG. 2: Crystal structure of example 2d2. The absolute configuration was determined by the anomalous scattering of the 'heavy' bromine atom.

DETAILED DESCRIPTION OF THE INVENTION

The compounds of the present invention contain two chiral centers (denoted with * in the below formula)

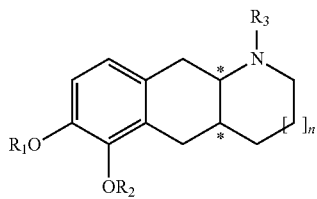

I

The compounds of the invention therefore can exist in two different diastereomeric forms, the cis- and trans-isomers, which forms both fall under the scope of the present invention.

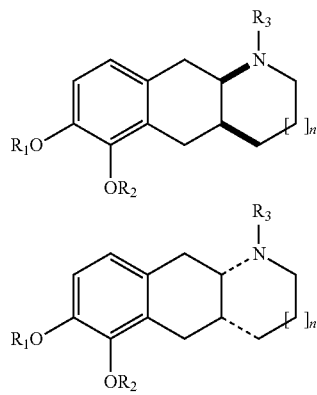

cis forms of the compounds of formula I

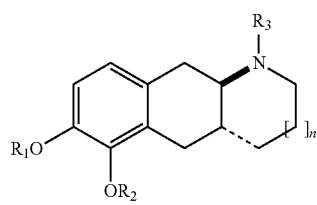

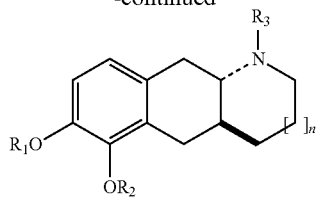

trans forms of the compounds of formula I

The ring-atoms of the compounds of the invention are numbered as follows:

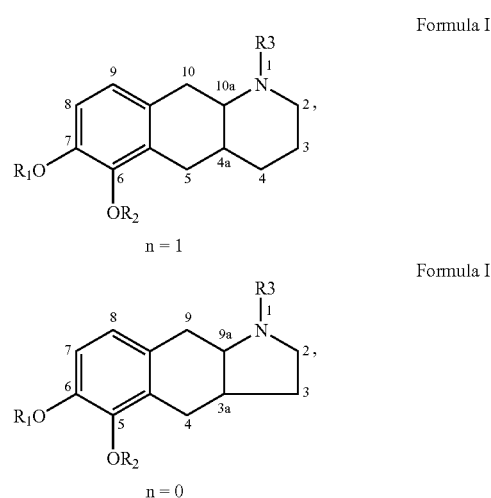

The diastereomeric forms further comprise two enantiomeric forms each, which means that the compounds of Formula I overall exist as the individual (R,R), (R,S), (S,S) and (S,R) enantiomers.

The compounds of Formula I have been found to behave like orally active Apomorphine-analogues, which render them potentially useful in relation to treatment of Parkinson's disease and other diseases/disorders, which responds favorably to an increased dopaminergic turnover.

A specific embodiment of the present invention relates to the use of a compound of Formula I or a pharmaceutically acceptable addition salt thereof for improving cognition in a mammal in a condition of cognitive impairment wherein the condition is associated with schizophrenia. In another embodiment of the invention the condition is associated with Parkinson's Disease. In another embodiment of the invention the condition is associated with dementia, such as AIDS dementia. In another embodiment of the invention the condition is associated with an anxiety disorder. In another embodiment of the invention the condition is associated with age associated memory impairment. In another embodiment of the invention the condition is associated with depression, including major depression, in particular in elderly. In another embodiment of the invention the condition is associated with the use of benzodiazepines. In another embodiment of the invention the condition is associated with the use of tricyclic antidepressants. In another embodiment of the invention the condition is associated with Alzheimer's Disease. In another embodiment of the invention the condition is associated with attention deficit hyperactivity disorder (ADHD). In another embodiment of the invention the condition is associated with post-traumatic stress disorder (PTSD).

In a further embodiment the present invention relates to the use of a compound of Formula I or a pharmaceutically acceptable addition salt thereof for the treatment of dyskinesias in a mammal.

In another embodiment the present invention relates to the use of a compound of Formula I or a pharmaceutically acceptable addition salt thereof for the treatment of a mammal suffering from depression, such as major depression, bipolar disorder or anxiety.

According to the present invention an interesting neuropharmacological difference has been found between the two trans-enantiomers of underivatized catecholamines of Formula I ($R_1$ and $R_2$=H), which have been prepared in enantiomerically pure form by a process of the current invention. It has thus been demonstrated that the (4aR,10aR) enantiomers are potent, dual D1/D2 agonists with $EC_{50}$ values <200 nM [see the Experimental Section for a description of the in vitro assays used], whereas the (4aS,10aS) antipodes are much less potent D1 agonists, and only display moderately strong D2 agonism.

Some of the (4aR,10aR) enantiomers of compounds of Formula I have furthermore been tested for D5 affinity and have proven to be very potent D5 agonists with $EC_{50}$ values <10 nM.

The racemic compounds of Formula I for which n=1, $R_1$ and $R_2$=hydrogen and $R_3$=hydrogen, methyl, ethyl and n-propyl have previously been disclosed [see e.g. Cannon, Lee, Beres, Goldman; J. Heterocycl. Chem., 17, 1633 (1980)], and their dopaminergic activity discussed [see e.g. Bradbury, Costall, Naylor; Neuropharmacology 23(9), 1025 (1984); Bradbury, Cannon, Costall, Naylor; Eur. J. Pharmacol. 105 (1-2), 33 (1984)]. The racemic compound of Formula I for which n=1, $R_1$ and $R_2$=hydrogen and $R_3$=ethyl has been reported to stimulate both D1 and D2 receptors [Itoh, Goldman, Kebabain; Eur. J. Pharmacol., 108 (1), 99 (1985)]. However, none of these prior art documents discuss the enantioselectivity of the compounds of Formula I, or the different selectivities obtained in vitro vs. in vivo.

As mentioned previously, the compound Apomorphine is currently used clinically in PD therapy. Apomorphine is a mixed D1-like/D2-like agonist:

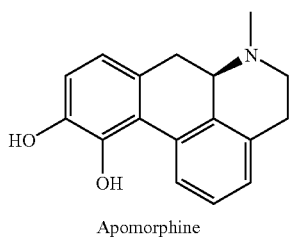

Apomorphine

When the compounds of the invention are tested in vitro and in vivo for their effect on D1 and D2 receptors, their pharmacological profiles are very different from that of Apomorphine (see Experimental Section for details)

It has been demonstrated that the D1/D2 selectivity ratio for the underivatized catecholamines of Formula I ($R_1$ and $R_2$=H) changes dramatically when comparing in vitro with in vivo measurements. In in vitro assays, these compounds are significantly more potent on D2 receptors than on D1 receptors (typically with a ratio of ~100). However, the in vivo ratio is shifted towards a 2-10 fold selectivity. Thus, it is evident that an extrapolation from in vitro data to the in vivo situation cannot be made for the compounds of the invention.

As mentioned previously, the presently available information supports the hypothesis that a D1-like agonist (be it selective for either subtype or a mixed D1/D5 agonist) could have important applications in the treatment of cognitive impairment in e.g. psychosis, PD, and Alzheimer's disease (AD), and Huntington's disease. This might well be the case also for dual action D1/D2 agonists, such as the compounds of Formula I.

In a particular embodiment, the invention therefore relates to substantially pure (4aR,10aR) enantiomers of compounds of Formula I wherein n=1, $R_1$ and $R_2$ are both hydrogen and $R_3$ is selected from the group consisting of hydrogen, methyl, ethyl, n-propyl, allyl, and propargyl.

In another embodiment, the invention relates to substantially pure (4aR,10aR) enantiomers of compounds of Formula I wherein n=1, $R_1$ and $R_2$ are both hydrogen and $R_3$ is n-propyl In another embodiment, the invention relates to substantially pure (4aR,10aR) enantiomers of compounds of Formula I wherein n=1, $R_1$ and $R_2$ are both hydrogen and $R_3$ is methyl In a separate embodiment, the invention relates to substantially pure (4aR,10aR) enantiomers of compounds of Formula I wherein n=1

The invention also relates to compounds of Formula I to be used as PET ligands or as intermediates therefore. The desired radiolabel can be introduced by the use of radiolabeled precursors, including $^{11}C$-labelled precursors such as [$^{11}C$]methyl iodide, [$^{11}C$]methyl triflate, etc. The compounds may also be labeled with $^3H$, $^{18}F$ or. In a specific embodiment of the invention is therefore provided a radiolabeled compound of Formula I in which the radiolabel is selected from $^{11}C$, $^3H$, $^{18}F$ or $^{113}I$.

The radiolabeled compounds of Formula I wherein $R_1$ and $R_2$ are both hydrogen are particularly preferred as radioligands.

In a specific embodiment, the invention relates to a radiolabeled compound of Formula I wherein n=1, $R_1$ and $R_2$ are both hydrogen and $R_3$ is 3-($^{18}F$)-fluoropropyl or 2-($^{18}F$)-fluoroethyl.

Another embodiment relates to the free base of a compound of Formula I, or a salt hereof, or a pharmaceutical composition hereof and the uses as described herein, wherein the compound of Formula I has a trans-diastereomeric excess of at least 10% (10% trans-diastereomeric excess means that the ratio of the trans- to the cis-diastereoisomer is 55:45 in the mixture in question), at least 25%, at least 50%, at least 70%, at least 80%, at least 90%, at least 95%, at least 97%, preferably at least 98%.

A further embodiment relates to the free base of a compound of Formula I, or a salt hereof, or a pharmaceutical composition hereof and the uses as described herein, wherein the compound of Formula I has an enantiomeric excess of at least 10% (for example, 10% enantiomeric excess for a compound of Formula I having (4aR,10aR) configuration means that the ratio between the (4aR,10aR)- and (4aS,10aS)-enantiomers is 55:45 in the mixture in question), at least 25%, at least 50%, at least 70%, at least 80%, at least 90%, at least 95%, at least 97%, preferably at least 98%.

In another aspect the present invention comprises compounds of Formula I wherein the catechol moiety is masked as a methylenedioxy (MDO) prodrug derivative, which may be cleaved in vivo (most likely by in vivo metabolism) to generate the active catecholamines (exemplified below for n=1):

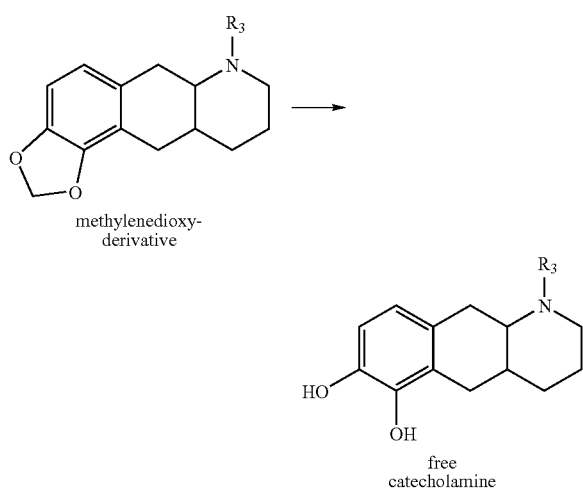

methylenedioxy-
derivative free
catecholamine

The invention thus also relates to compounds of Formula I wherein $R_1$ and $R_2$ are fused and form a methylene ($CH_2$) group.

In another aspect the present invention also comprise such compounds of Formula I wherein the catechol moiety is masked as a di-ester derivative which may also be cleaved in vivo to generate the active catecholamines (exemplified below for n=1, and $R_1$ and $R_2$=acetyl):

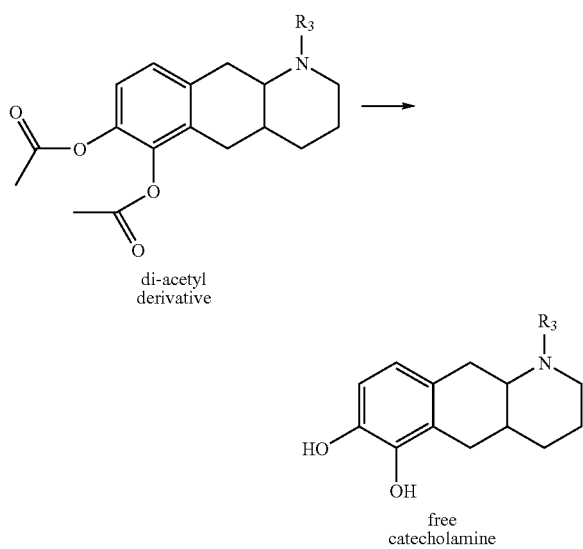

di-acetyl
derivative free
catecholamine

The present invention further comprises unsymmetrical di-ester derivatives of the compounds of Formula I, wherein $R_1$ and $R_2$ are two different substituents. The present invention also comprises compounds wherein $R_1$ and $R_2$ are fused and form a carbonyl (C=O) group, such that a cyclic di-ester (a carbonate) is produced.

The invention furthermore relates to substantially pure trans-diastereoisomers of compounds of Formula I wherein n=0, $R_1$ and $R_2$ are fused and form a methylene ($CH_2$) group, and $R_3$ is selected from the group consisting of hydrogen and methyl, ethyl, n-propyl The invention also relates to substantially pure (4aR,10aR) enantiomers of compounds of Formula I wherein n=1, $R_1$ and $R_2$ are fused and form a methylene ($CH_2$) group, and $R_3$ is selected from the group consisting of hydrogen, methyl, ethyl and n-propyl.

In separate embodiments the invention relates to compounds of Formula I wherein $R_3$ is selected from the group consisting of hydrogen, methyl, ethyl and n-propyl and at least one of $R_1$ and $R_2$ is $C_{1-6}$ alkanoyl, or at least one of $R_1$ and $R_2$ is benzoyl, or at least one of $R_1$ and $R_2$ is phenylacetyl.

The invention furthermore relates to substantially pure trans-diastereoisomers of Formula I wherein $R_3$ is selected from the group consisting of hydrogen, methyl, ethyl and n-propyl and at least one of $R_1$ and $R_2$ is $C_{1-6}$ alkanoyl such as pivaloyl, or at least one of $R_1$ and $R_2$ is benzoyl, or at least one of $R_1$ and $R_2$ is phenylacetyl.

The invention also relates to substantially pure (4aR,10aR) enantiomers of Formula I wherein $R_3$ is selected from the group consisting of hydrogen, methyl, ethyl and n-propyl and at least one of $R_1$ and $R_2$ is $C_{1-6}$ alkanoyl such as pivaloyl, or at least one of $R_1$ and $R_2$ is benzoyl, or at least one of $R_1$ and $R_2$ is phenylacetyl.

In the present context, in particular for the pharmaceutical uses, it is understood that when specifying the compound of Formula (I) to be substantially enantiomerically or diastereomerically pure, then the compound is relatively stereochemically pure, preferably the enantiomeric or diastereomeric excess is at least 60%, at least 70%, and more preferably at least 80% (80% enantiomeric excess means that the ratio of eg. (4aR,10aR) to (4aS,10aS) is 90:10 in the mixture in question), at least 90%, at least 96%, or preferably at least 98%.

Experimental Section
General Methods

Analytical LC/MS data were obtained on a PE Sciex API 150EX instrument equipped with atmospheric pressure photo ionisation and a Shimadzu LC-8A/SLC-10A LC system. Purity was determined by integration of the UV (254 nm) and ELSD traces. MS instruments are from PESciex (API), equipped with APPI-source and operated in positive ion mode. The retention times in the UV-trace (RT) are expressed in min. Solvents A was made of 0.05% TFA in water, while solvent B was made of 0.035% TFA and 5% water in acetonitrile. Several different methods have been used:

Method 14: API 150EX and Shimadzu LC8/SLC-10A LC system. Column: C-18 4.6×30 mm, 3.5 μm (Symmetry, Waters). Column temperature: rt. Gradient: reverse phase with ion pairing. Flow: 2 mL/min. Injection volume: 10 micro-L. Gradient: 10% B in A to 100% B over 4 min then 10% B in A for 1 min. Total run time: 5 min.

Method 17: API 150EX and Shimadzu LC8/SLC-10A LC system. Column: C-18 4.6×30 mm, 4 μm (Phenomenex Synergi Hydro). Temperature: rt. Gradient: reverse phase with ion pairing. Flow: 2 mL/min. Injection volume: 10 micro-L. Gradient: 2% B in A to 100% B over 4 min then 10% B in A for 1 min. Total run time: 5 min.

Method 25: API 150EX and Shimadzu LC10AD/SLC-10A LC system. Column: dC-18 4.6×30 mm, 3 μm (Atlantis, Waters). Column temperature: 40° C. Gradient: reverse phase with ion pairing. Flow: 3.3 mL/min. Injection volume: 15 micro-L. Gradient: 2% B in A to 100% B over 2.4 min then 2% B in A for 0.4 min. Total run time: 2.8 min.

Method 101: API 150EX and Shimadzu LC8/SLC-10A LC system. Column: C-18 4.6×30 mm, 3.5 μm (Symmetry, Waters). Column temperature: 60° C. Gradient, reverse phase with ion pairing. Flow: 3.3 mL/min. Injection volume: 15 micro-L. Gradient: 10% B in A to 100% B over 2.4 min then 10% B in A for 0.4 min. Total run time: 2.8 min.

Method 102: API 150EX and Shimadzu LC8/SLC-10A LC system. Column: dC-18 4.6×30 mm, 3 μm (Atlantis, Waters).

Column temperature: 40° C. Gradient, reverse phase with ion pairing. Flow: 3.3 mL/min. Injection volume: 15 micro-L. Gradient: 2% B in A to 100% B over 2.4 min then 2% B in A for 0.4 min. Total run time: 2.8 min.

Method 111: API 150EX and Shimadzu LC8/SLC-10A LC system. Column: C-18 4.6×30 mm, 3.5 μm (Symmetry, Waters). Column temperature: 60° C. Gradient, reverse phase with ion pairing. Flow: 3.3 mL/min. Injection volume: 10 micro-L (1 micro-L injected onto the column). Gradient: 10% B in A to 100% B over 2.4 min then 10% B in A for 0.4 min. Total run time: 2.8 min.

Method 314: API 150EX and Shimadzu LC8/SLC-10A LC system. Column: C-18 4.6×30 mm, 3.5 μm (Symmetry, Waters). Column Temperature: rt. Flow 2 mL/min. Injection volume: 10 micro-L. Gradient: 10% B in A over 4 min then 100% B for 0.1 min then 10% B for A in 0.9 min. Total run time: 5.0 min.

Method 23 SUN: API 150EX and Shimadzu LC8/SLC-10A LC system. Column: C-18 4.6×30 mm, 3.5 μm (Sunfire, Waters). Column temperature: 40° C. Gradient, reverse phase with ion pairing. Flow: 3.3 mL/min. Injection volume: 15 micro-L. Gradient: 10% B in A to 100% B over 2.4 min then 10% B in A for 0.4 min. Total run time: 2.8 min.

Preparative LC/MS-purification was performed on the same instrument with atmospheric pressure chemical ionisation. Column: 50×20 mm YMC ODS-A with 5 μm particle size. Method: linear gradient elution with 80% A to 100% B in 7 min and with a flow rate of 22.7 mL/min. Fraction collection was performed by split-flow MS detection.

Hydrogenation reactions were performed using either a standard Parr shaker or an Endavour instrument from Argonaut. In all cases, low pressure was used (1-5 bar hydrogen pressure).

The term "silica gel chromatography (EtOAc/heptane)" has the following meaning: The compound to be purified was usually dissolved in a small amount of DCM and loaded onto a column pre-packed with silica gel and eluted using a mixture of EtOAc and heptane, either in a isocratic fashion or with a gradient such as 0-100% of EtOAc in heptane. One example of a column loaded with silica gel used is "ISOLUTE SPE COLUMNS" [e.g. 20 g FLASH Si 70 ml from International sorbent technology]. Alternatively, classical manual chromatographic purifications were performed using silica gel [e.g. Machery-Nagel 60 M; 0.04-0.063 mm, 230-400 mesh] with compound identification by standard TLC analysis performed on aluminium plates precoated with silica gel [e.g. Merck 60 $F_{254}$]. Compounds were visualized by illumination using a UV lamp (254 nm) or by charring after dipping in a solution of ammonium molybdate (6.25 g) and cerium(IV)sulfate (2.5 g) in 10% aqueous sulphuric acid (250 mL).

Microwave-accelerated reactions were performed in sealed microwave reactor vials. The experiments were performed on a Smith Synthesizer from Personal Chemistry.

The term "lyophilized" refers to the freeze-drying of a material using a Christ Alpha 2-4 LSC instrument from WWR International.

The terms "dried ($Na_2SO_4$)" and "dried ($Mg_2SO_4$)" refers to the removal of water from organic layers by the addition of dry $Na_2SO_4$ or $Mg_2SO_4$, respectively, followed by stirring for an appropriate amount of time to ensure an effective drying process. Then the solid is removed by filtration, and the filtrate is typically concentrated in vacuo (see below).

The term "concentrated in vacuo" has the following meaning: The volatiles were removed from the mixture using a standard rotary evaporator at reduced pressure. The term "dried in vacuo at 40° C." refers to the use of a standard vacuum oven heated to 40° C. connected to an oil pump. The term "dried in vacuo" refers to a drying process in which the material to be dried is placed in a flask connected directly to an oil pump for a sufficient period of time to remove volatile components.

X-ray crystal structure determinations were performed as follows. The crystal of the compounds was cooled to 120 K using a Cryostream nitrogen gas cooler system. The data were collected on a Siemens SMART Platform diffractometer with a CCD area sensitive detector. The structures were solved by direct methods and refined by full-matrix least-squares against $F^2$ of all data. The hydrogen atoms in the structures could be found in the electron density difference maps. The non-hydrogen atoms were refined anisotropically. All the hydrogen atoms were at calculated positions using a riding model with O—H=0.84, C—H=0.99-1.00, N—H=0.92-0.93 Å. For all hydrogen atoms the thermal parameters were fixed [U(H)=1.2 U for attached atom]. The Flack x-parameters are in the range 0.0(1)-0.05(1), indicating that the absolute structures are correct. Programs used for data collection, data reduction and absorption were SMART, SAINT and SADABS [cf. "SMART and SAINT, Area Detector Control and Integration Software", Version 5.054,Bruker Analytical X-Ray Instruments Inc., Madison, USA (1998), Sheldrick "SADABS, Program for Empirical Correction of Area Detector Data" Version 2.03, University of Göttingen, Germany (2001)]. The program SHELXTL [cf. Sheldrick "SHELXTL, Structure Determination Programs", Version 6.12, Bruker Analytical X-Ray Instruments Inc., Madison, USA (2001)] was used to solve the structures and for molecular graphics.

General Synthetic Methods for Markush Structures
Ia and Ib

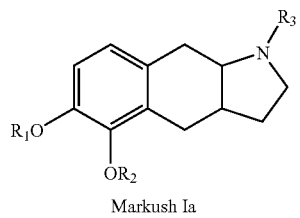

Markush Ia

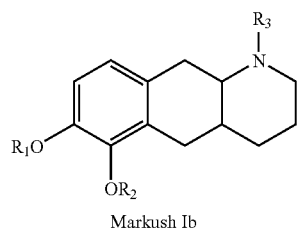

Markush Ib

Markush Structure Ia

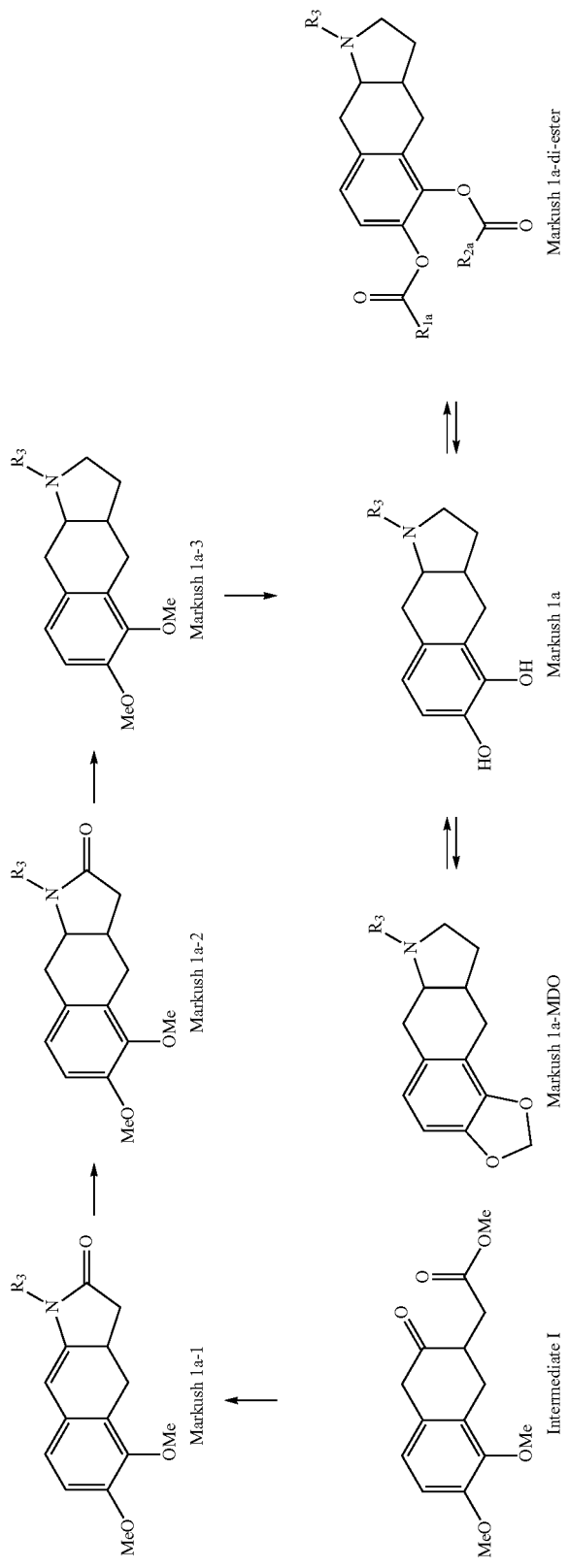

Starting from intermediate I, whose synthesis is described herein, condensation with primary amine $R_3NH_2$ gives Markush 1a-1 under the conditions herein for the synthesis of compound 25 from intermediate I. Reduction of Markush 1a-1 with LAH provides Markush 1a-2 e.g. under the conditions herein for the synthesis of compounds 13 and 14. After separation of the cis/trans mixture, either diastereomer can be treated with 48% HBr or a related reagent to cleave the methoxy groups to furnish Markush 1a e.g. under the conditions described herein for the synthesis of example 1a1. Further reaction of Markush 1a with $CH_2ClBr$ or a related reagent in the presence of base to give Markush 1a-MDO e.g. under the conditions described herein for the synthesis of example 3b1. The resulting Markush 1a-MDO can be converted back to Markush 1a by treatment with $BCl_3/(n\text{-}Butyl)_4NI$ or a related reagent. Markush 1a can be converted to Markush 1a-di-ester by treatment with the appropriate acid chloride(s) in TFA to give Markush 1a-di-ester e.g. as described herein for the synthesis of example 4a1. This material can be hydrolyzed to Markush 1a.

Markush Structure Ib example 2f1 or reductive amination e.g. under the conditions described herein for the conversion of intermediate II to example 2h1 can be used to obtain trans-Markush 1b-1. This masked catecholamine can be deprotected under standard conditions by treatment with 48% HBr e.g. under the conditions described herein for the synthesis of example 2c1 or by reaction with $BBr_3$ e.g. under the conditions described herein for the conversion of intermediate II to example 2g1 to give trans-Markush 1b. Further reaction with $CH_2ClBr$ or a related reagent in the presence of base can be applied to give trans-Markush 1b-MDO e.g. under the conditions described herein for the synthesis of example 3b1. The resulting trans-Markush 1b-MDO can be converted back to trans-Markush 1b by treatment with $BCl_3/(n\text{-}Butyl)_4NI$ or a related reagent. An alternative strategy involves acylation of intermediate II to trans-Markush 1b-2 which can be reduced to trans-Markush 1b-1 with LAH or a related reagent e.g. under the conditions described herein for the synthesis of example 2e1 to target trans-Markush 1b and trans-Markush 1b-MDO analogs in which $R_3$ can be defined as $CH_2R$. Treatment of trans-Markush 1b with the appropriate acid chloride(s) in TFA can be used to prepare trans-Markush 1b-di-ester e.g. as

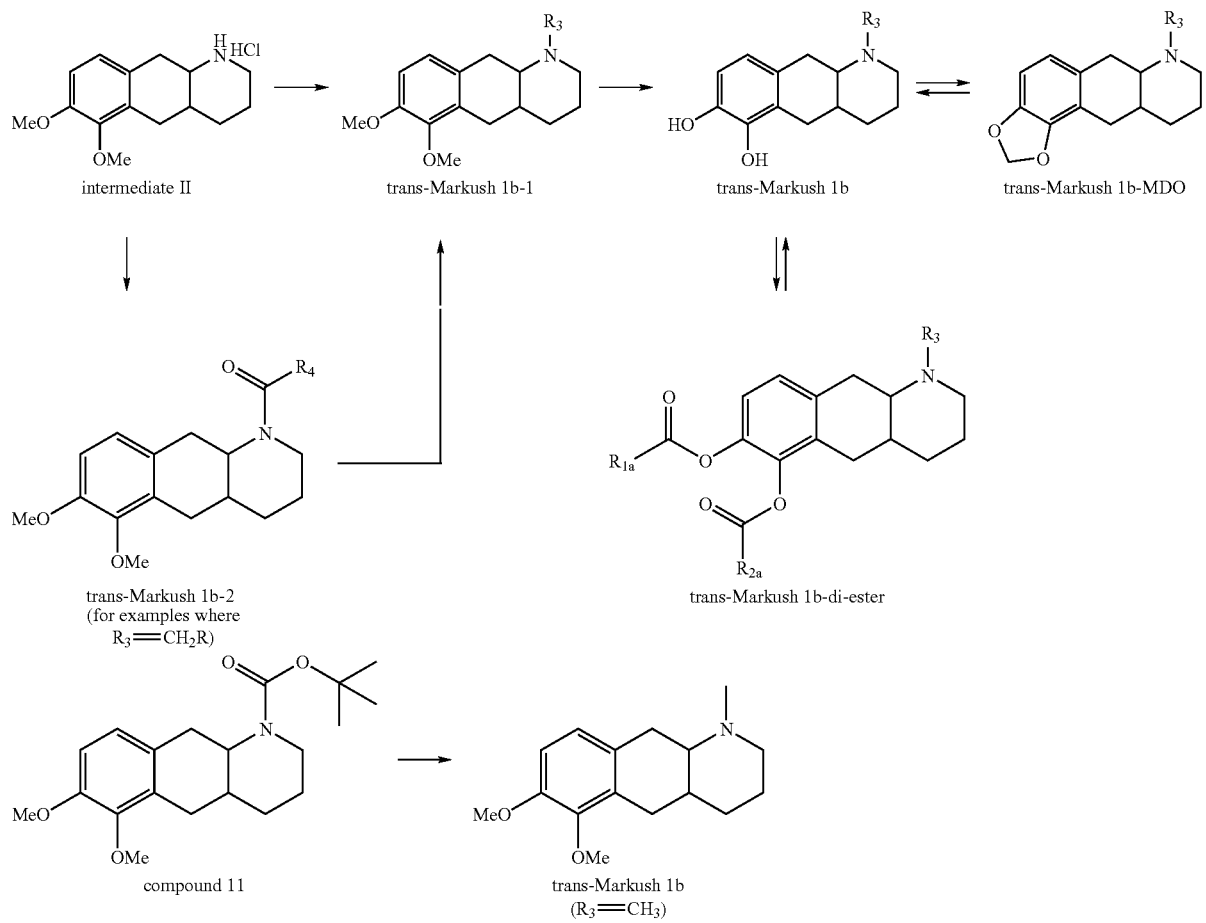

Starting from trans-configured intermediate II, whose synthesis is described herein (the enantiomeric series can be prepared from intermediate III whose synthesis is also described herein), direct N-alkylation e.g. under the conditions described herein for the conversion of intermediate II to described herein for the synthesis of example 4a1. These di-esters trans-Markush 1b-di-ester can be hydrolyzed to the parent catecholamines trans-Markush 1b. Molecules trans-Markush 1b in which $R_3=CH_3$ can be prepared from compound 11 (using its pure enantiomers compound 11A and compound 11B can be used to the prepare optically products) by treatment with LAH or a related reagent e.g. under the conditions described herein for the synthesis of example 2b1; subsequently the resulting trans-Markush 1b-1 is transformed to trans-Markush 1b, trans-Markush 1b-MDO, or trans-Markush 1b-di-ester as described before.

Markush 1b-MDO. An alternative strategy involves acylation of example 3a1 to trans-Markush 1b-3, which can be reduced with LAH or a related reagent e.g. under the conditions described herein for the conversion of intermediate II to example 2e1 to target trans-Markush 1b-MDO analogs in

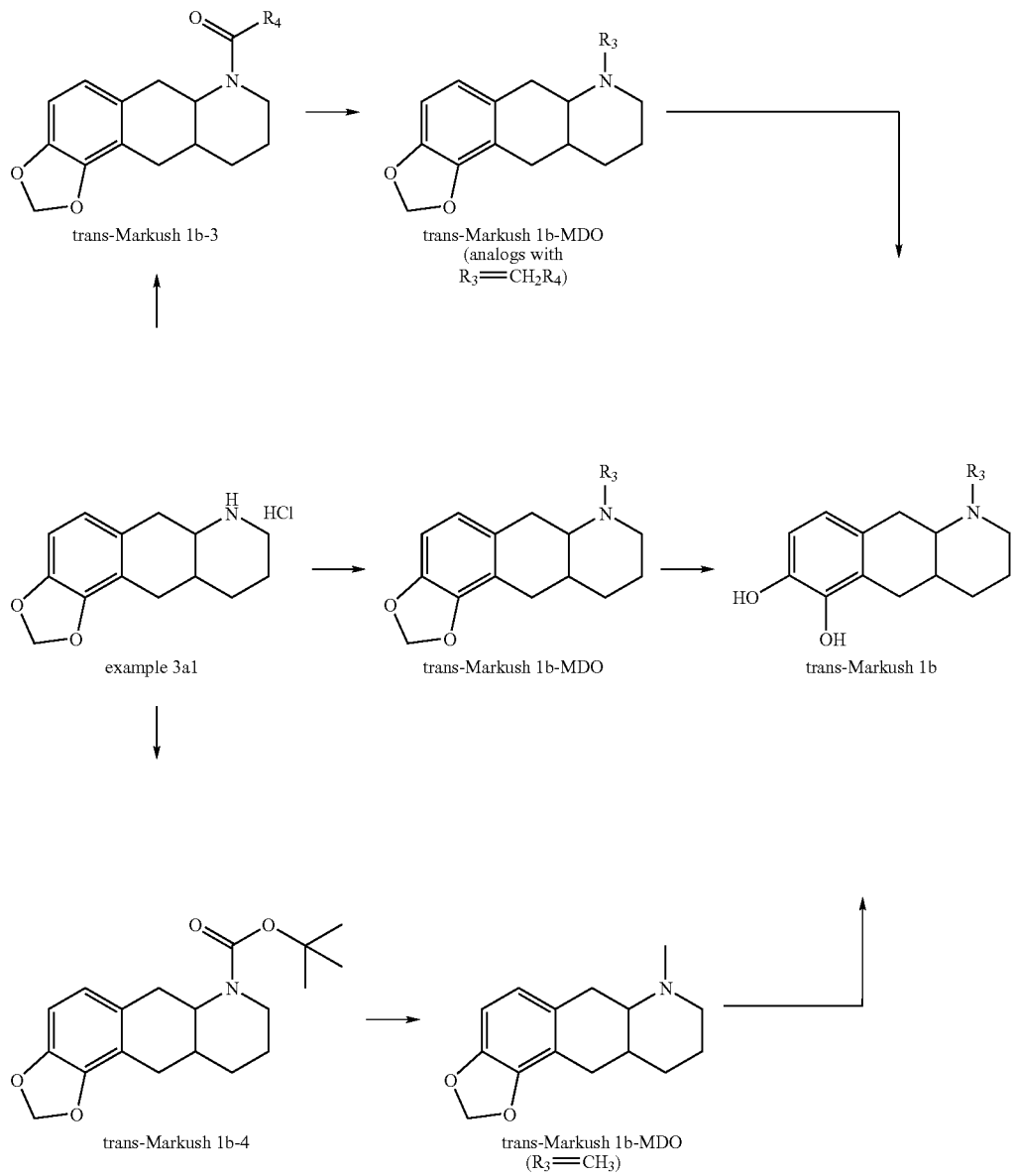

Starting from trans-configured example 3a1, whose synthesis from intermediate II is described herein (the enantiomeric series can be prepared from intermediate III whose synthesis is also described herein), direct N-alkylation e.g. under the conditions described herein for the conversion of intermediate II to example 2f1 or reductive amination e.g. under the conditions described herein for the conversion of intermediate II to example 2h1 can be used to obtain trans- which $R_3$ can be defined as $CH_2R_4$. Furthermore, example 3a1 can be Boc-protected e.g. under the conditions reported herein for the synthesis of compound 8 to afford trans-Markush 1b-4, which can be reduced with LAH or a related reagent to target trans-Markush 1b-MDO analogs in which $R_3$=$CH_3$. For trans-Markush 1b-MDO treatment with e.g. $BCl_3$/(n-Butyl)$_4$NI can be used to give trans-Markush 1b.

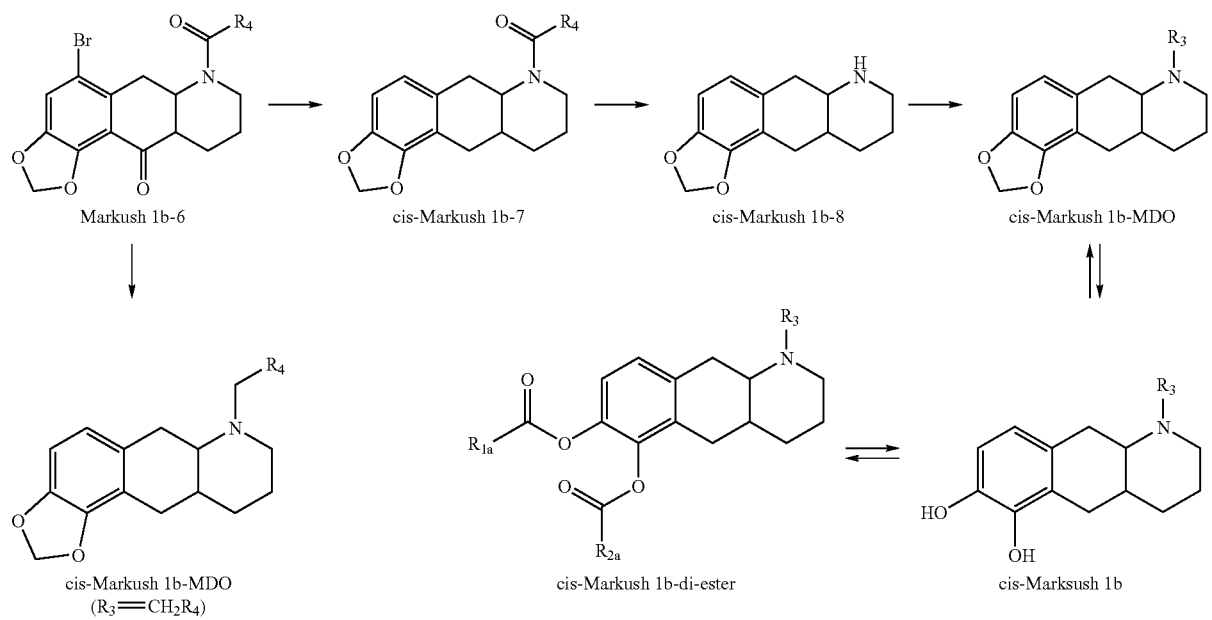

Starting from Markush 1b-6 (for a synthesis of such a compound, see the description of the synthesis of compound 25 herein), treatment with e.g. Pd/C and hydrogen gas can be used to obtain cis-Markush 1b-7. Cleavage of the amide group can afford cis-Markush 1b-8. Direct N-alkylation e.g. under the conditions described herein for the conversion of intermediate II to example 2f1 or reductive amination e.g. under the conditions described herein for the conversion of intermediate II to example 2h1 can be used to obtain cis-Markush 1b-MDO. As for the trans-series described above, treatment with e.g. $BCl_3$/(n-Butyl)$_4$NI can be used to give cis-Markush 1b, which can be converted back to cis-Markush 1b-MDO by reaction with $CH_2ClBr$ or a related reagent in the presence of base to give cis-Markush 1b-MDO e.g. under the conditions described herein for the synthesis of example 3b1. Treatment of cis-Markush 1b material with the appropriate acid chloride(s) in TFA can be used to prepare cis-Markush 1b-di-ester e.g. as described herein for the synthesis of example 4a1. These di-esters can be hydrolyzed to the parent catecholamines cis-Markush 1b. Reduction of cis-Markush 1b-8 can be used to prepare cis-Markush 1b-MDO analogs in which $R_3$ can be defined as $CH_2R_4$ as described herein.

Useful Intermediates for the Preparation of Compounds of the Invention

The following intermediates are useful in the preparation of the compounds of the invention:

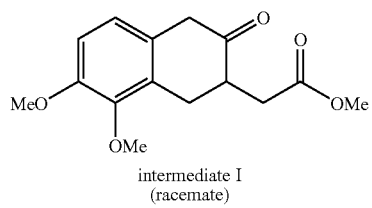

intermediate I
(racemate)

-continued

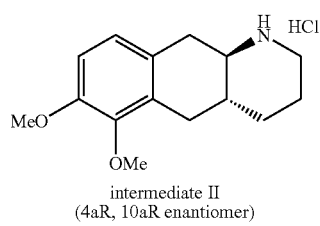

intermediate II
(4aR, 10aR enantiomer)

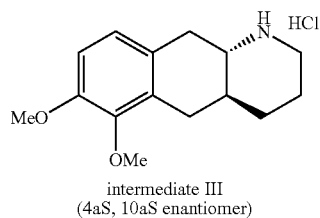

intermediate III
(4aS, 10aS enantiomer)

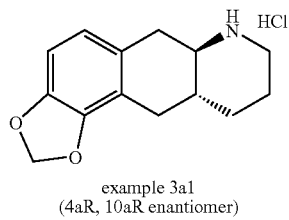

example 3a1
(4aR, 10aR enantiomer)

In the following sections general synthetic methods for the preparation of the intermediates will be presented followed by specific examples.

General Procedure for Preparation of benzo[f]indole catecholamines

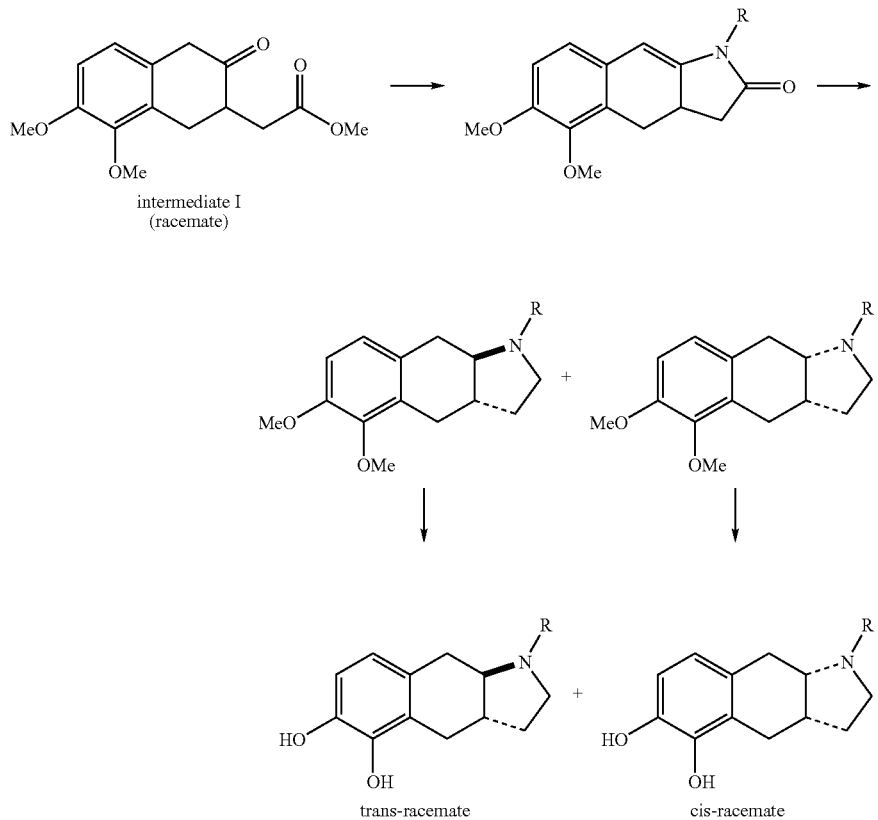

Intermediate I, whose synthesis is described herein, is reacted with a primary amine and the resulting enamine-lactam is then reduced by alane and then sodium borohydride. This produces a mixture of the cis/trans protected benzo[f]indole catechol amines. These diastereomers are separated, for example by silica gel chromatography [for an example of a closely related synthesis, see: Lin, Haadsma-Svensson, Phillips, Lahti, McCall, Piercey, Schreur, von Voigtlander, Smith, Chidester; J. Med. Chem., 36(8), 1069 (1993)]. The masked catecholamine is liberated e.g. by treatment with 48% HBr or with BBr$_3$.

Preparation of Intermediate I

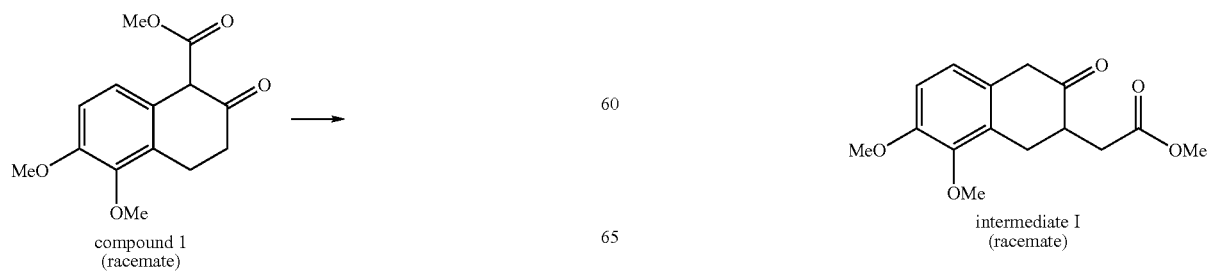

Racemic 3-Allyl-5,6-dimethoxy-3,4-dihydro-1H-naphthalen-2-one (Compound 2)

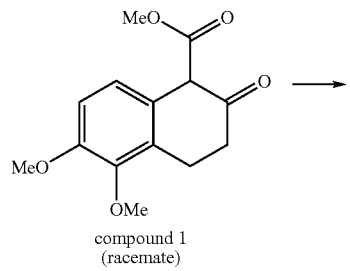
compound 1
(racemate)

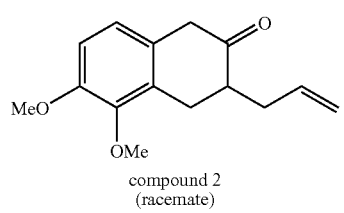
compound 2
(racemate)

A solution of racemic 5,6-dimethoxy-2-oxo-1,2,3,4-tetrahydro-naphthalene-1-carboxylic acid methyl ester (6.60 g) [compound 1; prepared as described in Taber, Neubert, Rheingold; J. Am. Chem. Soc., 124(42), 12416 (2002)] in THF (25 mL) was added drop-wise to a solution of LDA (27 mL, 2M in THF/heptane/ethylbenzene) in THF (125 mL) at 0° C. The solution was stirred at 0° C. for 1.5 h. Allyl bromide (3.44 mL) was added and the solution was stirred at rt overnight. Et$_2$O (300 mL) and 1 M HCl (300 mL) were added and the layers were separated. The organic layer was washed with brine, dried (MgSO$_4$) and concentrated in vacuo. The residual oil was dissolved in DMSO (25 mL) and water (2.5 mL) and LiCl (1 g) was added. The reaction mixture was stirred at 150° C. for 0.5 h and then cooled to rt. EtOAc (250 mL) and water (250 mL) were added and the layers were separated. The aqueous layer was extracted with EtOAc (125 mL). The combined organic layers were washed with brine, dried (MgSO$_4$) and concentrated in vacuo. The crude product was purified by silica gel chromatography (EtOAc/heptane) to give 2.55 g of compound 2 as a white solid.

Racemic 3'-Allyl-5',6'-dimethoxy-3',4'-dihydro-1'H-spiro[[1,3]dioxolane-2,2'-naphthalene](Compound 3)

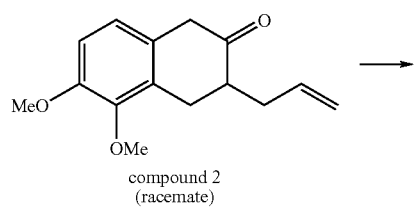
compound 2
(racemate)

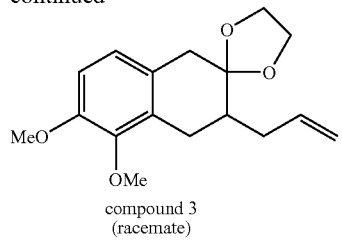
compound 3
(racemate)

CH(OCH$_3$)$_3$ (4.53 mL), ethylene glycol (5.68 mL) and PTSA (20 mg) were added to a stirred solution of compound 2 (2.55 g) in DCM (45 mL). The solution was stirred at rt for 4.5 h, and then quenched by adding sat. aq. NaHCO$_3$ (45 mL). The organic layer was washed with brine, dried (MgSO$_4$) and concentrated in vacuo. The crude product was purified by silica gel chromatography (EtOAc/heptane) to give 2.52 g of compound 3 as an oil.

Racemic 3-Allyl-5,6-dimethoxy-3,4-dihydro-1H-naphthalen-2-one (Intermediate I)

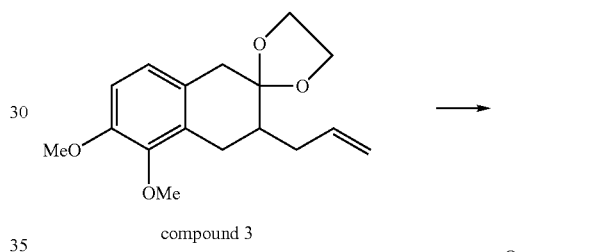
compound 3 intermediate I

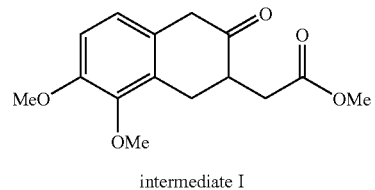
compound 3
(racemate)

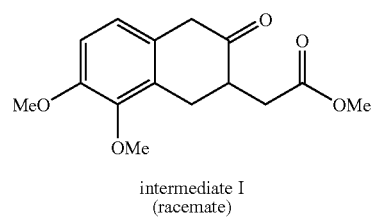
intermediate I
(racemate)

KMnO$_4$ (4.75 g) was added to a stirred solution of NaIO$_4$ (98 g) in water (1.7 L) at rt. The solution was stirred for 0.5 h after which K$_2$CO$_3$ (12.7 g) and the solution was stirred for an additional 5 min. A solution of compound 3 (14.8 g) in t-butyl alcohol (500 mL) was added. The solution was stirred 3 h and then cooled on an ice/water bath. Sodium hydrogen sulfite (38-40% aqueous solution) was added drop-wise over 0.5 h. DCM (1 L) was added and the layers were separated. The aqueous layer was extracted with more DCM (0.4 L) and the combined organic layers were washed with brine, dried (MgSO₄) and concentrated in vacuo to produce 11.3 g of a dark oil. This material was dissolved in acetonitrile (225 mL) and a solution of AcCl (37 mL) in MeOH (190 mL) was added. The solution was stirred 5 min at rt and then kept at 4° C. overnight, and then stirred 2 h at rt. Water (45 mL) was added and the solution was stirred for 3 h after which it was concentrated in vacuo. The crude residue was purified by silica gel chromatography (EtOAc/heptane) to give 3.62 g of intermediate I as an oil.

General Procedure for Preparation of benzo[g]quinoline catecholamines

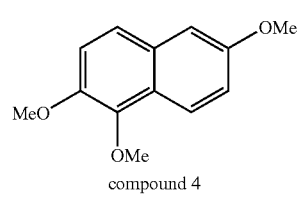

compound 4

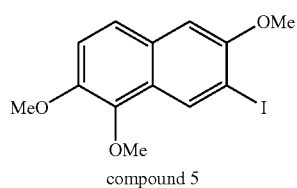

compound 5 six steps

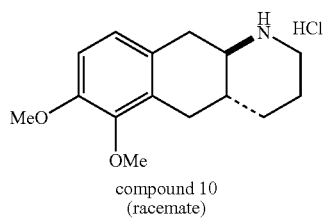

compound 10
(racemate)

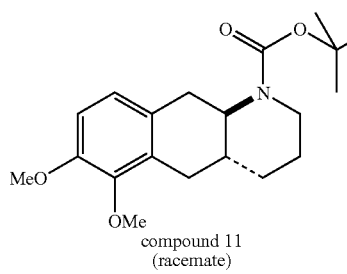

compound 11
(racemate)

SFC
(resolution)

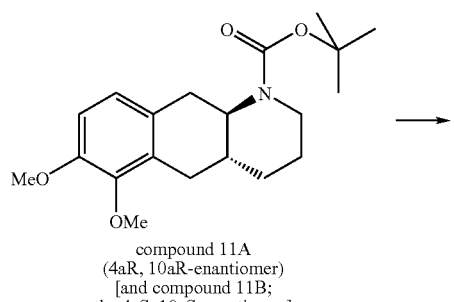

compound 11A
(4aR, 10aR-enantiomer)
[and compound 11B;
the 4aS, 10aS-enantiomer]

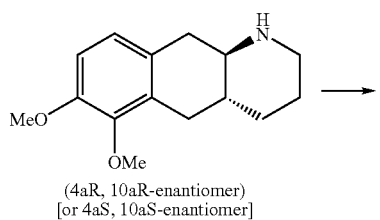

(4aR, 10aR-enantiomer)
[or 4aS, 10aS-enantiomer]

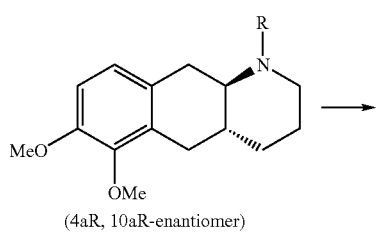

(4aR, 10aR-enantiomer)
[or 4aS, 10aS-enantiomer]

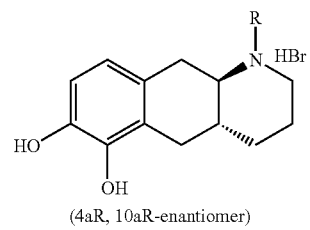

(4aR, 10aR-enantiomer)

Regioselective lithiation of 1,2,6-trimethoxynaphthalene [which can be prepared as described in Taber, Neubert, Rheingold; J. Am. Chem. Soc., 124(42), 12416 (2002)] followed by treatment with $I_2$ e.g. under the conditions described herein for the synthesis of compound 5 furnishes a substrate for a Heck coupling with acrylonitrile following a literature procedure for a closely related compound [Mellin, Hacksell; Tetrahedron, 43(22), 5443 (1987)]. After an additional five steps as described herein it is possible to obtain the key intermediate II. This material can be resolved using SFC on a preparative scale. The two enantiomers are then deprotected, and the nitrogen atom is functionalized using either by direct alkylation, reductive amination, or a two-step acylation/reduction. Finally, the masked catecholamine is liberated under standard conditions by treatment with 48% HBr or with $BBr_3$.

Preparation of Intermediates II and III
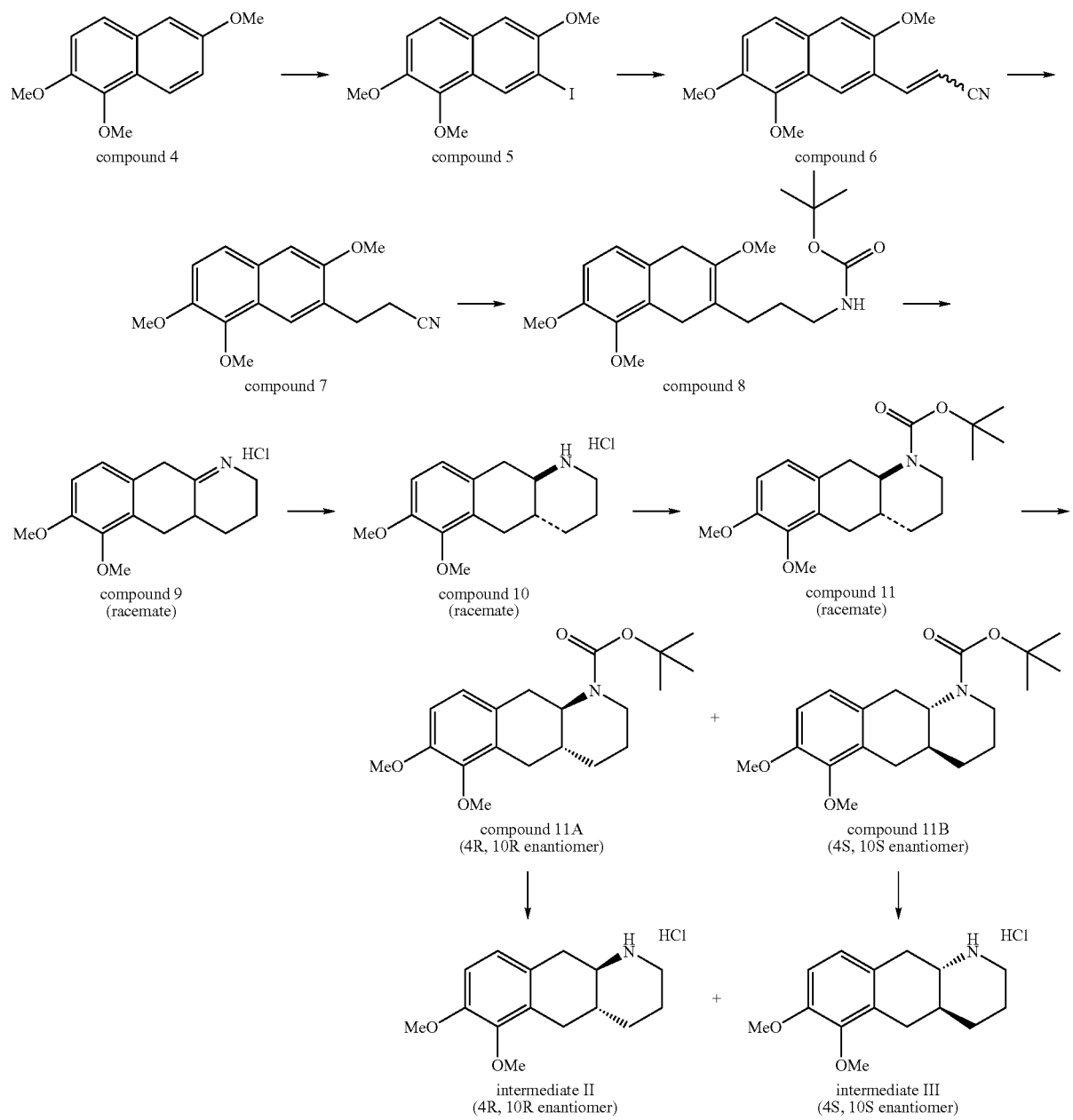
7-Iodo-1,2,6-trimethoxy-naphthalene (Compound 5)
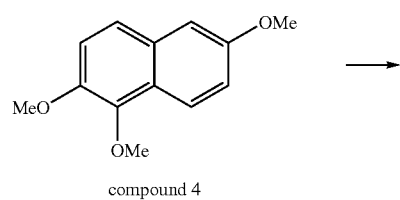
To a stirred solution of compound 4 (26.2 g; prepared as described in Taber, Neubert, Rheingold; J. Am. Chem. Soc., 124(42), 12416 (2002)) in dry THF (200 mL) under argon and at −78° C. was slowly added s-butyl lithium (1.2 M in cyclo-hexane, 110 mL). The solution was stirred at −78° C. for 3 h. A solution of iodine (30.5 g) in dry THF (50 mL) was added over a period of 10 min. The resulting mixture was then stirred for another 10 min at −78° C. The reaction mixture was quenched by the addition of sat. NH₄Cl (100 mL), water (240 mL), and Et₂O (240 mL). The organic layer was washed with 10% aqueous sodium sulfite solution (100 mL), dried (Na₂SO₄) and concentrated in vacuo. The crude material was purified by distilling off unreacted starting material. The residue was further purified by silica gel chromatography (EtOAc/heptane) to produce an impure solid material, which was purified by precipitation from EtOAc/heptane affording 11.46 g of compound 5.

(E/Z)-3-(3,7,8-Trimethoxy-naphthalen-2-yl)-acrylonitrile (Compound 6)

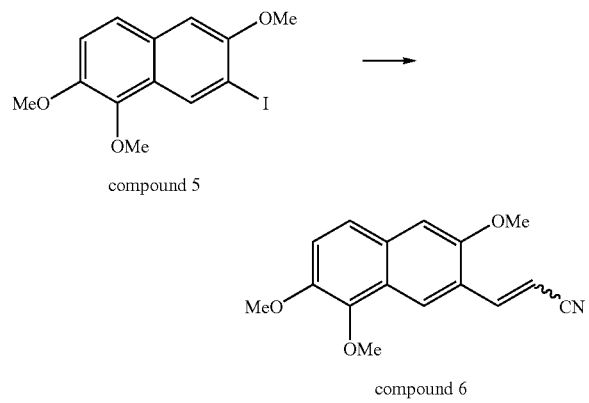

To a suspension of compound 5 (3.41 g) in dry acetonitrile (10.7 mL) in a microwave reactor vial was added acrylonitrile (1.19 mL) Pd(OAc)₂ (73 mg), and triethylamine (1.48 mL). The vial was sealed, and the mixture was heated for 40 min at 145° C. under microwave irradiation. This procedure was carried out two more times (using a total of 10.23 g of compound 5). The crude reaction mixtures were combined and the catalyst was filtered off, and the filtrate was concentrated in vacuo. The residue was partitioned between Et₂O (300 mL) and 2M HCl (150 mL). The organic layer was washed with brine (100 mL), dried (Na₂SO₄) and concentrated in vacuo. The crude material (7.34 g) was purified by silica gel chromatography (EtOAc/heptane) to produce 5.23 g of compound 6 as a mixture of olefin isomers.

3-(3,7,8-Trimethoxy-naphthalen-2-yl)-propionitrile (Compound 7)

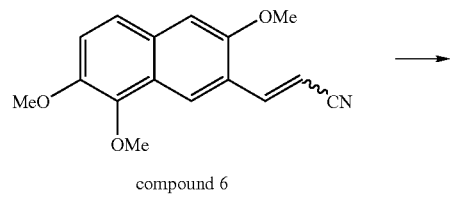

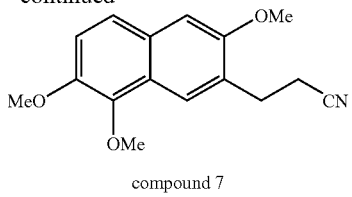

Compound 6 (5.23 g) was dissolved in CHCl₃ (15 mL) and 99% EtOH (100 mL). 10% Pd/C (0.8 g) was added and the solution was hydrogenated for 45 min under a hydrogen pressure of 3 bar using a Parr shaker. The catalyst was filtered off, and the filtrate was passed through a small plough of silica gel (eluent: 99% EtOH). Yield: 4.91 g compound 7 as a white solid.

[3-(3,7,8-Trimethoxy-1,4-dihydro-naphthalen-2-yl)-propyl]-carbamic acid t-butyl ester (Compound 8)

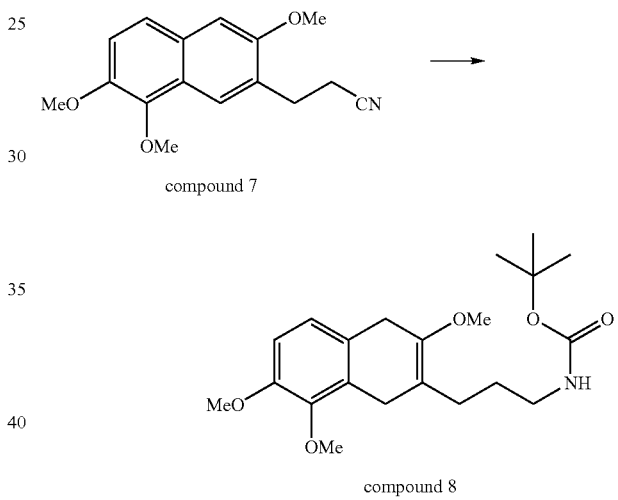

Compound 7 (5.0 g) was dissolved in 99% EtOH (150 mL) and the mixture was heated to reflux under nitrogen atmosphere. Sodium metal (5 g) was added in small lumps over 3 h. The mixture was refluxed for an addition 2 h, before it was stirred at rt for 2 days. Then it was heated to reflux again, and more sodium metal (3.68 g) was added and the mixture was refluxed overnight. After cooling on an ice/water bath, the reaction was quenched by the addition of solid ammonium chloride (20 g) and water (25 mL). The resulting mixture was filtered, and the filtrate was concentrated in vacuo. The residue was partitioned between diethyl ether (50 mL) and water (50 mL). The aqueous layer was neutralized with 37% HCl and extracted with diethyl ether (2×50 mL). The combined organic extracts were washed with brine (50 mL), dried (MgSO₄) and concentrated in vacuo to afford an oil. This material was dissolved in THF (50 mL) and treated with Boc₂O (2.34 g) and Et₃N (1.78 mL) at rt. After six days the volatiles were removed in vacuo and the residue was purified by silica gel chromatography (EtOAc/heptane). This provided impure compound 8 (1.52 g).

Racemic 6,7-dimethoxy-2,3,4,4a,5,10-hexahydro-benzo[g]quinoline hydrochloride (Compound 9)

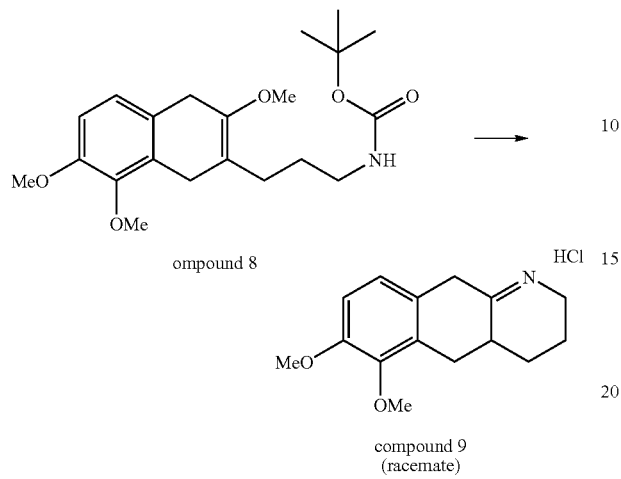

Compound 8 (1.52 g from the previous step) was dissolved in MeOH (20 mL). 37% HCl (3.5 mL) was added, and the mixture was refluxed for 4 h. The volatiles were removed in vacuo, using toluene to azeotropically remove the water. This provided impure compound 9 (0.89 g) as an yellow oil.

Racemic trans-6,7-dimethoxy-3,4,4a,5,10,10a-hexahydro-2H-benzo[g]quinoline-1-carboxylic acid t-butyl ester (Compound 11)

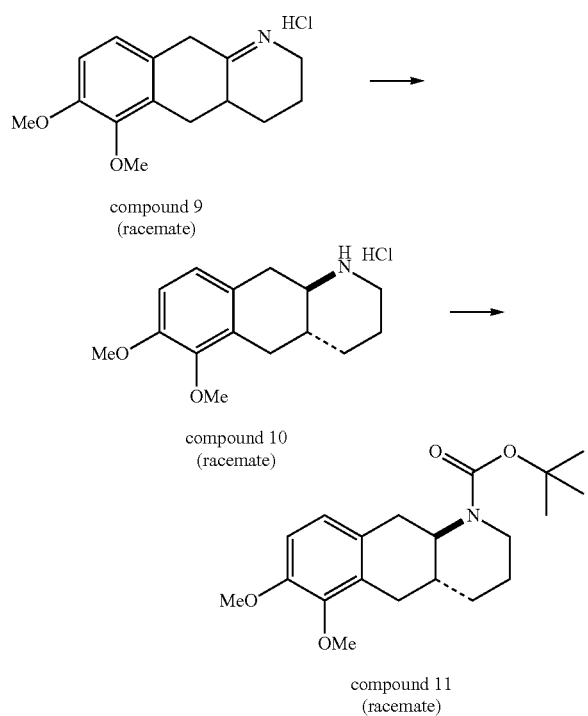

Compound 9 (0.89 g) was dissolved in MeOH (10 mL) and NaCNBH$_3$ (0.19 g) was added. The reaction was stirred overnight at rt. The crude mixture was cooled on an ice/water bath, before it was quenched with 2 M HCl in Et$_2$O (1 mL). The mixture was partitioned between Et$_2$O (50 mL), water (50 mL), and 2 M NaOH (10 mL). The aqueous layer was extracted with diethyl ether (3×50 mL). The combined organic layers were dried (MgSO$_4$) and concentrated in vacuo to afford the impure free amine (compound 10). This material was dissolved in THF (25 mL) and treated with Boc$_2$O (0.68 g) and Et$_3$N (0.86 mL) at rt for 1 h. The crude mixture was concentrated in vacuo, and the residue was purified by silica gel chromatography (EtOAc/heptane) to provide 1.18 g of slightly impure racemic compound 11.

SFC-Separation of the enantiomers of racemic trans-6,7-dimethoxy-3,4,4a,5,10,10a-hexahydro-2H-benzo[g]quinoline-1-carboxylic acid t-butyl ester (Compounds 11A and 11B)

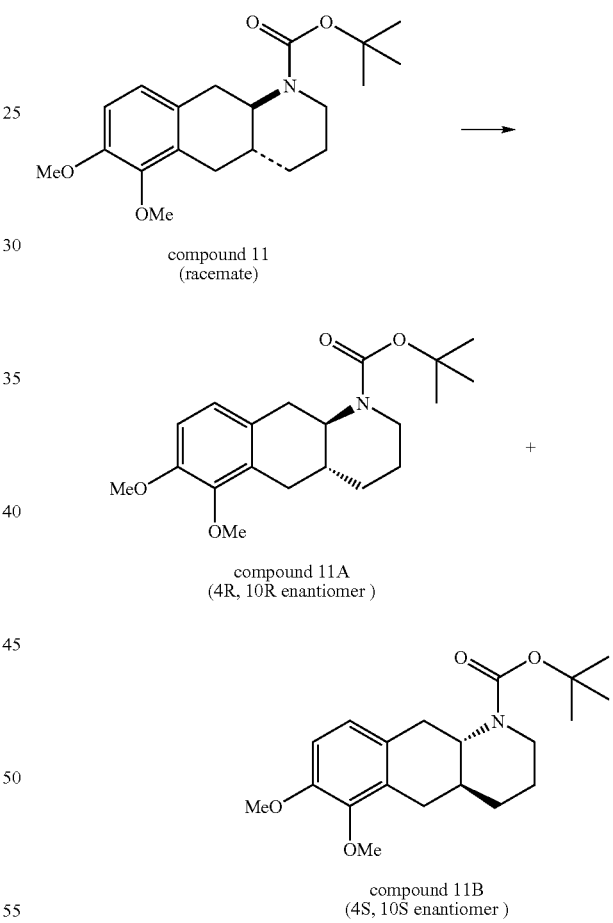

Compound 11 (19.7 g) was resolved into its enantiomers using chiral SFC on a Berger SFC multigram II instrument equipped with a Chiralcel OD 21.2×250 mm column. Solvent system: CO$_2$/EtOH (85:15), Method: constant gradient with a flow rate of 50 mL/min. Fraction collection was performed by UV 230 nm detection. Fast eluting enantiomer (4aR,10aR enantiomer; compound 11A): 9.0 g of a white solid. Slow eluting enantiomer (4aS,10aS enantiomer; compound 11B): 8.1 g of a white solid.

(4aR,10aR)-6,7-Dimethoxy-1,2,3,4,4a,5,10,10a-octahydro-benzo[g]quinoline hydrochloride (Intermediate II)

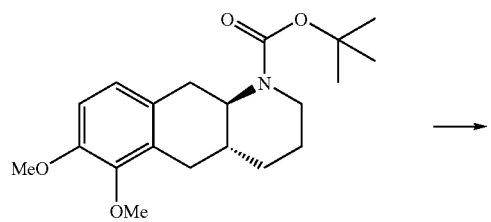

compound 11A
(4R, 10R enantiomer)

intermediate II
(4R, 10R enantiomer)

Compound 11A (0.54 g) dissolved in MeOH (15 mL) was treated with 5 M HCl in Et$_2$O 7.5 (mL) at rt for 2 h. The mixture was concentrated in vacuo and the solid was dried in vacuo to give 0.44 g of intermediate II as a white solid.

(4aS,10aS)-6,7-Dimethoxy-1,2,3,4,4a,5,10,10a-octahydro-benzo[g]quinoline hydrochloride (Intermediate III)

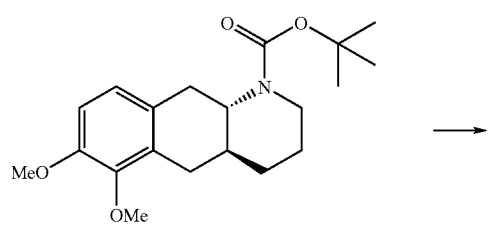

(4S, 10S enantiomer)
compound 24B (4S, 10S enantiomer)
intermediate III

The procedure described for Intermediate II above was followed using the enantiomeric starting material (compound 11B; 0.52 g) to give 0.38 g of intermediate III as a white solid. LC/MS (method 14): RT 1.31 min.

Determination of the Absolute Configuration of Intermediates II and III

The absolute configuration of example 2d2 was determined by X-ray crystallography and allowed for unambiguous determination of the stereochemistry of intermediates II and III and hence their derivatives.

General Procedure for the Preparation of MDO-catecholamines

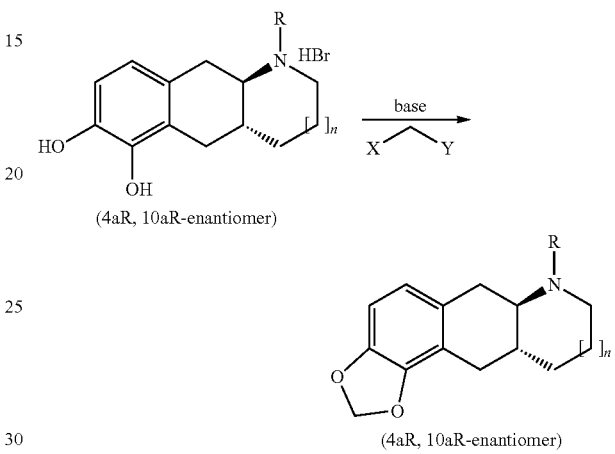

(4aR, 10aR-enantiomer)

(4aR, 10aR-enantiomer)

n = 0, 1
Same procedure for the (4aS, 10aS)-enantiomer

The catechol amine hydrobromide is treated with CH$_2$BrCl or a similar reagent in the presence of base to give the methylene-di-oxy (MDO) catecholamine [for general references on this transformation, see for example: Gensler, Samour; J. Org. Chem., 18(1), 9, (1953); Cabiddu, Cadoni, De Montis, Fattuoni, Melis, Usai; Tetrahedron, 59(24), 4383 (2003); for references with catecholamines, see: Ram, Neumeyer; J. Org. Chem., 46(13), 2830 (1981); Nichols, Brewster, Johnson, Oberlender, Riggs; J. Med. Chem., 33(2), 703 (1990)].

General Procedure for Conversion of catecholamines to diacyl catecholamines

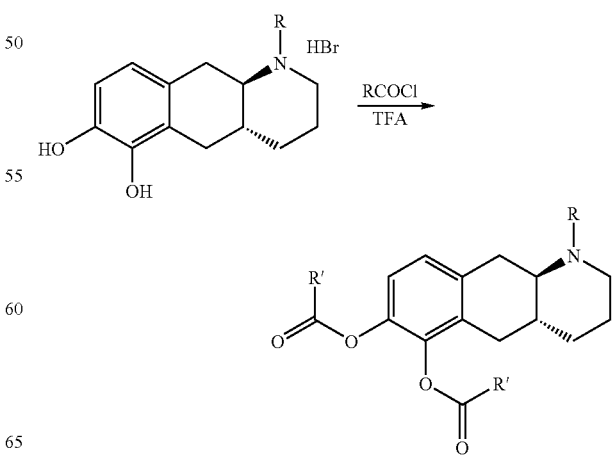

The catechol amine hydrobromide is treated with acylchloride using TFA as solvent. The crude diacyl catecholamines is purified by aluminium oxide chromatography [for a reference on this transformation, see for example: Wikström, Dijkstra, Cremers, Andren, Marchais, Jurva; WO 02/14279 A1, New aporphine esters and their use in therapy].

Preparation of Compounds 12-17

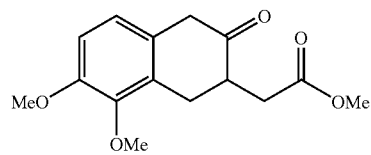

Intermediate I
(racemate)

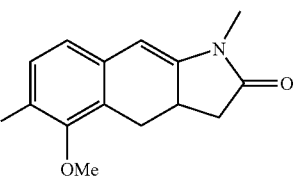

compound 12
(racemate)

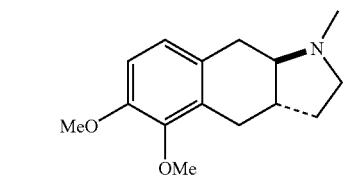

compound 13
(racemate)

compound 14
(racemate)

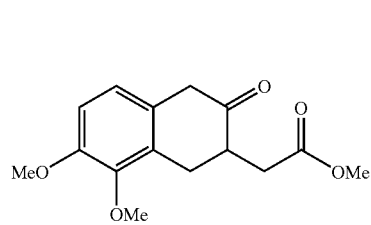

Intermediate I
(racemate)

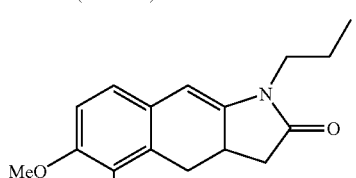

compound 15
(racemate)

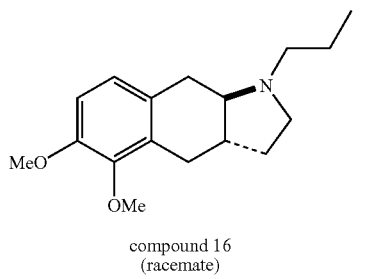

compound 16
(racemate)

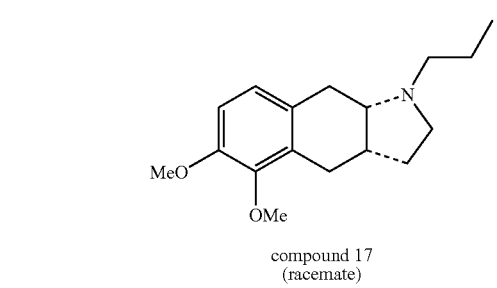

compound 17
(racemate)

Racemic 5,6-dimethoxy-1-methyl-1,3,3a,4-tetrahydro-benzo[f]indol-2-one (Compound 12)

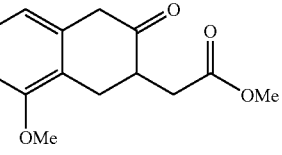

Intermediate I
(racemate)

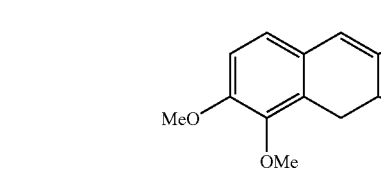

compound 12
(racemate)

To a stirred solution of Intermediate I (830 mg) in toluene (7 mL) in a microwave reactor vial was added a solution of methylamine (0.75 mL, 8 M in EtOH) and AcOH (0.34 mL) was added. The reactor was sealed and the mixture was heated at 120° C. for 15 min under microwave irradiation. The solution was concentrated in vacuo and the residue was dried in vacuo. The crude product was purified by silica gel chromatography (EtOAc/heptane). Yield: 210 mg of compound 12 as an oil.

Racemic trans- and cis-isomers of 5,6-dimethoxy-1-methyl-2,3,3a,4,9,9a-hexahydro-1H-benzo[f]indole (Compounds 13 and 14)

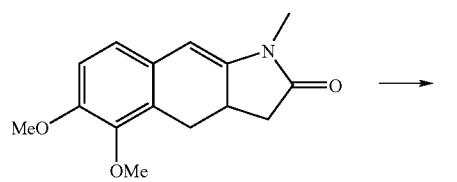

compound 12
(racemate)

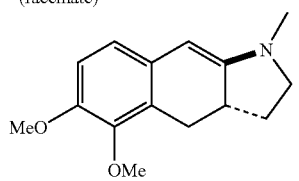

compound 13
(racemate)

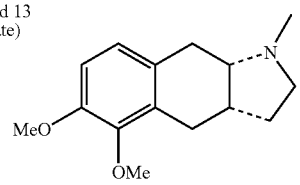

compound 14
(racemate)

To a stirred solution of LAH (3.9 mL, 1M in THF) at 0° C. was added AlCl₃ (174 mg). The mixture was allowed to warm to rt and then cooled to 0° C. again. To this mixture was added compound 12 (200 mg) dissolved in THF (4 ml) and the mixture was stirred at rt 1 h. The mixture was cooled to 0° C. and then quenched by adding wet Na₂SO₄. Inorganic salts there filtered off and the filtrate was concentrated in vacuo. The residue was dissolved in 99% EtOH and NaBH₄ (146 mg) was added, and the solution was stirred at rt overnight. The reaction mixture was quenched by adding 2M aqueous HCl (3 mL). Most of the volatiles were removed by concentration in vacuo and the residue was extracted with Et₂O. The organic layer was extracted with more dilute HCl. The combined dilute HCl layers were basified with 9 M NaOH and then extracted with Et₂O. The organic layer was washed with brine, dried (Na₂SO₄) and concentrated in vacuo. The crude mixture was purified by silica gel chromatography (MeOH/EtOAc). Yield: 4 mg of compound 13 as an oil (slow eluting isomer), and 32 mg of compound 14 as an oil (fast eluting isomer).

Racemic 5,6-dimethoxy-1-n-propyl-1,3,3a,4-tetrahydro-benzo[f]indol-2-one (Compound 15)

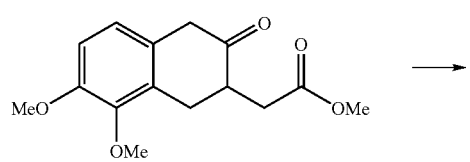

Intermediate I
(racemate)

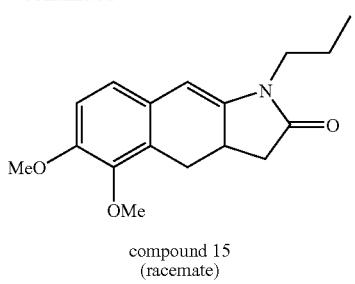

compound 15
(racemate)

Prepared from intermediate I (1.39 g) according to the procedure described for compound 12 using n-propyl amine instead of methyl amine. Yield of compound 15: 0.69 g as a solid.

Racemic trans- and cis-isomers of 5,6-dimethoxy-1-n-propyl-2,3,3a,4,9,9a-hexahydro-1H-benzo[f]indole (Compounds 16 and 17)

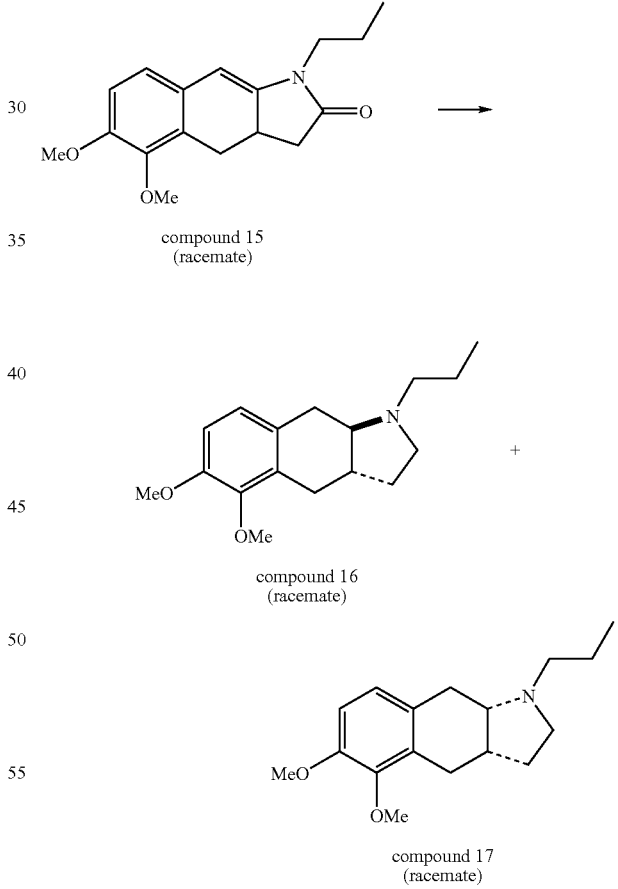

Compounds 16 and 17 were prepared in a similar manner as compounds 13 and 14 from compound 15 (400 mg) instead of compound 12. The crude product mixture was purified by silica gel chromatography (MeOH/EtOAc). Yield: 55 mg of compound 16 as an oil (slow eluting isomer), and 40 mg of compound 17 as an oil (fast eluting isomer).

Preparation of Compound 25

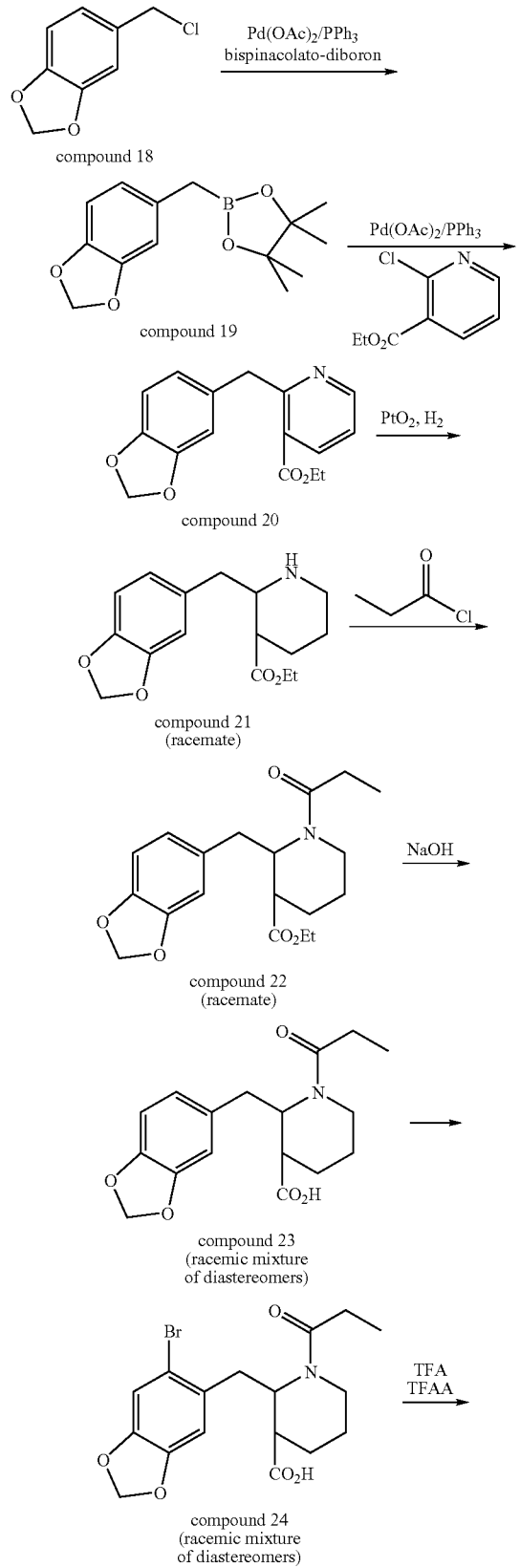

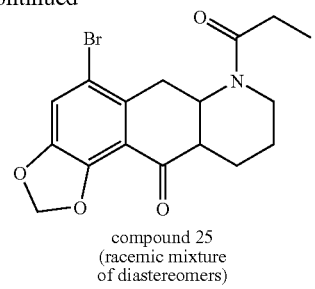

compound 25
(racemic mixture of diastereomers)

5-(4,4,5,5-Tetramethyl-[1,3,2]dioxaborolan-2-ylm-ethyl)-benzo[1,3]dioxole (Compound 19)

5-Chloromethyl-benzo[1,3]dioxole (12.7g; compound 18) whose whose synthesis is described in the literature [see e.g. Bourry, Akue-Gedu, Rigo, Henichart, Sanz, Couturier; J. Heterocycl. Chem., 40, 989 (2003)] is mixed with bispinacolato-diboron (18.9 g), potassium phosphate (47.4 g), palladium(II)acetate (0.17 g), and triphenyl phosphine (0.59 g) in a flask. 1,4-Dioxane (100 mL) is added, and the mixture is heated to reflux overnight. The crude mixture is filtered, and the filter cake is washed with a little EtOAc. The filtrate is washed with sat. aqueous $NaHCO_3$ and sat. aqueous NaCl, dried ($Na_2SO_4$), and concentrated in vacuo. The residue is dissolved in DCM and filtered through silica gel to afford compound 19 as an oil (14.4 g).

2-Benzo[1,3]dioxol-5-ylmethyl-nicotinic acid ethyl ester (Compound 20)

Compound 19 (31 g) was dissolved in DMF (300 mL). To the solution was added ethyl 2-chloro-nicotinate (11.6 mL), triphenyl phosphine (3.1 g), palladium(II)acetate (0.9 g), and potassium phosphate (51 g). The resulting mixture was heated to 80° C. overnight. Then, more ethyl 2-chloro-nicotinate (1.6 mL) was added, and the mixture was heated to 100° C. for ~24 h. The crude mixture was cooled to rt, and the inorganic solid was filtered off. The filtrate was partitioned between EtOAc and sat. aqueous $NH_4Cl$. The organic layer was extracted with 1M aqueous HCl. The aqueous layer was basified with 25% aqueous $NH_3$ and extracted with EtOAc. The organic layer was dried ($Na_2SO_4$) and concentrated in vacuo. The residue was purified by silica gel chromatography (heptane/EtOAc) to give impure compound 20 (4.5 g) as an oil.

2-Benzo[1,3]dioxol-5-ylmethyl-piperidine-3-carboxylic acid ethyl ester (Compound 21)

Compound 20 (1.0 g) was dissolved in AcOH (3 mL) and hydrogenated (1 bar) over $PtO_2$ at rt overnight. The catalyst was filtered off using celite, and the filtrate was concentrated in vacuo. The residue was portioned between 2M aqueous NaOH and DCM. The organic layer was dried ($MgSO_4$) and concentrated in vacuo to afford compound 21 (0.85 g) as an oil.

2-Benzo[1,3]dioxol-5-ylmethyl-1-propionyl-piperidine-3-carboxylic acid ethyl ester (Compound 22)

Compound 21 (0.84 g) was dissolved in DCM (10 mL) before DIPEA (1.0 mL) and propionyl chloride (0.3 mL) were added. The mixture was stirred at rt for 1.5 h, before the reaction was quenched by the addition of a few drops of 37% aqueous HCl and water. The crude mixture was partitioned between DCM and sat. aqueous NaHCO$_3$. The organic layer was dried (MgSO$_4$) and concentrated in vacuo to afford compound 22 (0.97 g).

2-(6-Bromo-benzo[1,3]dioxol-5-ylmethyl)-1-propionyl-piperidine-3-carboxylic acid (Compound 24)

Compound 22 (0.87 g) was dissolved in THF (5 mL) and treated with 2M aqueous NaOH (10 mL) at 60° C. overnight. The crude mixture was extracted using 2-methyl-THF. The organic layer was stirred with 1M aqueous citric acid, before it was extracted with 2-methyl THF, dried (MgSO$_4$), and concentrated in vacuo to give compound 23 as a solid. This material was dissolved in DMF (10 mL) and treated with NBS (0.44 g) at rt for 2 h. The crude mixture is diluted with MTBE and washed twice with 1M aqueous HCl. The organic layer was dried (MgSO$_4$) and concentrated in vacuo to give compound 24 (0.67 g) as a solid.

5-Bromo-7-propionyl-6a,7,8,9,10,10a-hexahydro-6H-1,3-dioxa-7-aza-cyclopenta[a]anthracen-11-one (Compound 25)

Compound 24 (0.56 g) was suspended in TFAA (6 mL) and TFA (4 mL) was added. The mixture was stirred at 80° C. for 5 h. The reaction was quenched with ice/27% aqueous NaOH, and the product was extracted into 2-methyl-THF. The organic layer was washed with sat. aqueous NaHCO$_3$, dried (MgSO$_4$), and concentrated in vacuo to give compound 25 (0.34 g).

Preparation of the Compounds of the Invention

The invention disclosed herein is further illustrated by the following non-limiting examples:

1b1 Racemic trans-1-methyl-2,3,3a,4,9,9a-hexahydro-1H-benzo[f]indole-5,6-diol trifluoroacetate

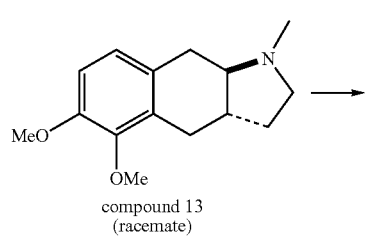

compound 13
(racemate)

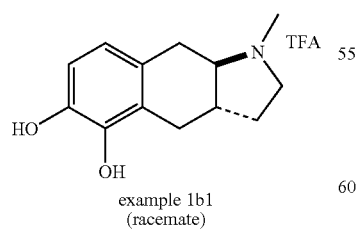

example 1b1
(racemate)

Compound 13 (4 mg) was suspended in 48% HBr (1 mL), and heated to 155° C. for 0.5 h in a sealed microwave reactor vial under microwave irradiation. The crude mixture was concentrated in vacuo, and the residue was purified by preparative LC/MS. Yield: 6 mg as a white solid. LC/MS (method 25): RT 0.52 min, ELSD 94.1%, UV 82.9%. MH$^+$: 220.3.

1b2 Racemic cis-1-methyl-2,3,3a,4,9,9a-hexahydro-1H-benzo[f]indole-5,6-diol trifluoroacetate

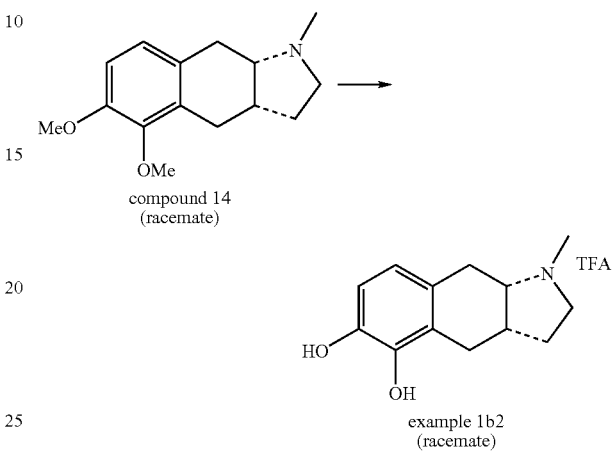

Compound 14 (32 mg) was suspended in 48% HBr (1.5 mL), and heated to 155° C. for 0.5 h in a sealed microwave reactor vial under microwave irradiation. The crude mixture was concentrated in vacuo, and the residue was purified by preparative LC/MS. Yield: 23 mg as a white solid. LC/MS (method 25): RT 0.52 min, ELSD 93.5%, UV 92.7%. MH$^+$: 220.2.

1d1 Racemic trans-1-n-propyl-2,3,3a,4,9,9a-hexahydro-1H-benzo[f]indole-5,6-diol trifluoroacetate

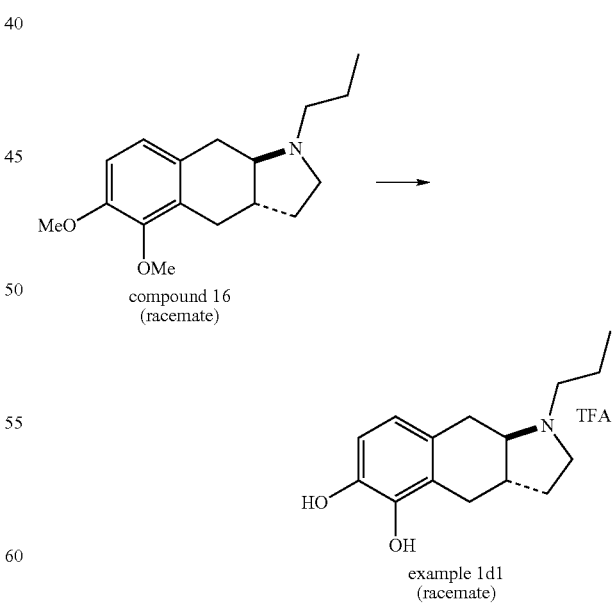

Compound 16 (55 mg) was suspended in 48% HBr (2 mL), and heated to 155° C. for 0.5 h in a sealed microwave reactor vial under microwave irradiation. The crude mixture was concentrated in vacuo, and the residue was purified by preparative LC/MS. Yield: 30 mg as a white solid. LC/MS (method 25): RT 0.69 min, ELSD 99.7%, UV 97.9%. MH+: 248.2.

1d2 Racemic cis-1-n-propyl-2,3,3a,4,9,9a-hexahydro-1H-benzo[f]indole-5,6-diol trifluoroacetate

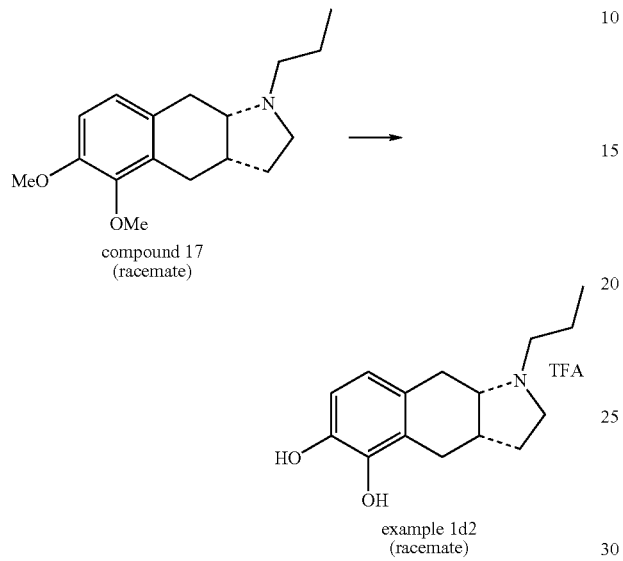

compound 17
(racemate)

example 1d2
(racemate)

Compound 17 (40 mg) was suspended in 48% HBr (2 mL), and heated to 155° C. for 0.5 h in a sealed microwave reactor vial under microwave irradiation. The crude mixture was concentrated in vacuo, and the residue was purified by preparative LC/MS. Yield: 8 mg as a white solid. LC/MS (method 25): RT 0.69 min, ELSD 99.1%, UV 97.8%. MH+: 248.3.

2a1 (4aR,10aR)-1,2,3,4,4a,5,10,10a-Octahydro-benzo[g]quinoline-6,7-diol hydrobromide

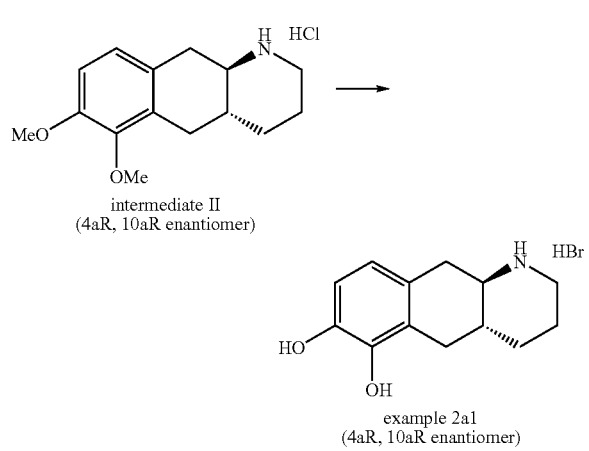

intermediate II
(4aR, 10aR enantiomer)

example 2a1
(4aR, 10aR enantiomer)

Intermediate II (19 mg) was placed in a microwave reactor vial and 48% HBr was added. The vial was sealed with a septum, and mixture was stirred at 160° C. for 0.5 h under microwave irradiation. The crude mixture was concentrated in vacuo, and the residue was purified by preparative LC/MS. Yield of example 2a1: 12.6 mg as a white solid. LC/MS (method 17): RT 1.48 min, ELSD 95.9%, UV 87.1%. MH+: 220.1.

2a2 (4aS,10aS)-1,2,3,4,4a,5,10,10a-Octahydro-benzo[g]quinoline-6,7-diol hydrobromide

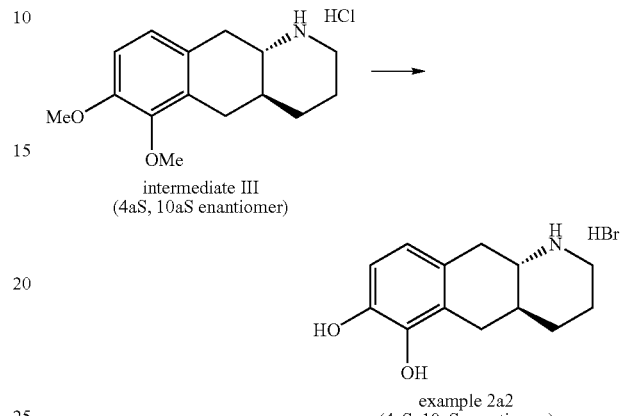

intermediate III
(4aS, 10aS enantiomer)

example 2a2
(4aS, 10aS enantiomer)

Intermediate III (16 mg) was placed in a microwave reactor vial and 48% HBr (1 mL) was added. The reactor was sealed, and the mixture was stirred at 170° C. for 1 h under microwave irradiation. The precipitated product was filtered off and dried in vacuo. Yield of example 2a2: 11 mg as a solid. LC/MS (method 17): RT 1.27 min, ELSD 88%, UV 75.1%, MH+: 220.1.

2b1 (4aR,10aR)-1-Methyl-1,2,3,4,4a,5,10,10a-octahydro-benzo[g]quinoline-6,7-diol hydrobromide

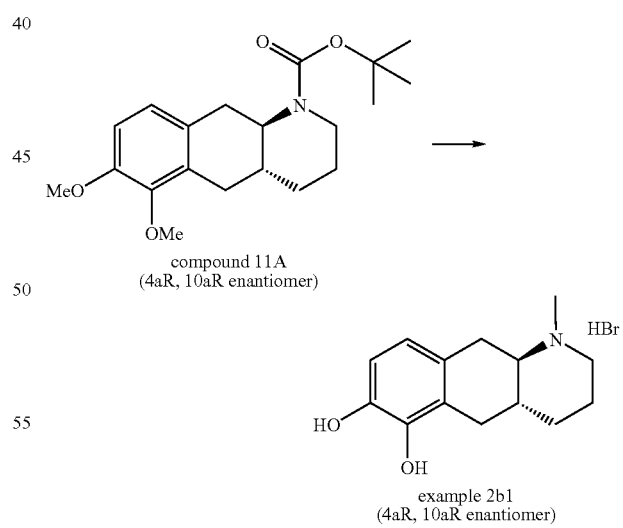

compound 11A
(4aR, 10aR enantiomer)

example 2b1
(4aR, 10aR enantiomer)

Compound 11A (3×270 mg) was added to three microwave vials followed by dry THF (7.75 mL) and LAH (1.0 M in THF; 2.3 mL). The vials were sealed and heated to 90° C. for 15 min. The three crude mixtures were poured into ice/water (30 mL), and the intermediate was extracted into Et$_2$O (3×50 mL). The combined organic extracts were washed with brine, dried (MgSO$_4$), and concentrated in vacuo. The residue was purified by silica gel chromatography (MeOH/EtOAc). The obtained intermediate was suspended in 48% HBr (4 mL) and treated at 150° C. under microwave conditions for 0.5 h. The precipitated material was isolated and stirred with MeOH (10 mL) at 85° C. under microwave conditions, and filtered to provide the product. Yield of example 2b1: 289 mg as a solid. LC/MS (method 25): RT 0.54 min, ELSD 98.2%, UV 93.8%, MH$^+$: 234.1.

2b2 (4aS,10aS)-1-Methyl-1,2,3,4,4a,5,10,10a-octahydro-benzo[g]quinoline-6,7-diol hydrobromide

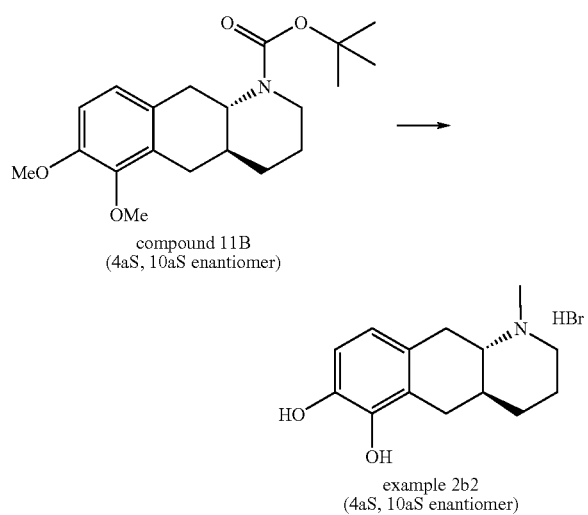

The procedure described for example 2b1 was followed starting from compound 11B (174 mg). Yield of example 2b2: 121 mg as a solid. LC/MS (method 17): RT 1.35 min, ELSD 99.4%, UV 100%, MH$^+$: 234.0.

2c1 (4aR,10aR)-1-Ethyl-1,2,3,4,4a,5,10,10a-octahydro-benzo[g]quinoline-6,7-diol hydrobromide

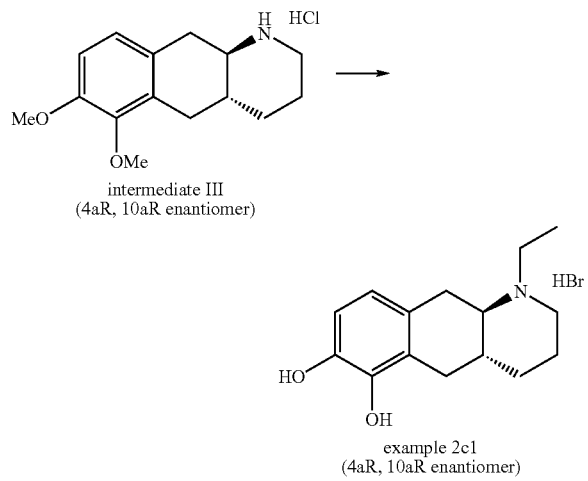

AcCl (0.13 g) and Et$_3$N (0.34 g) were added to a suspension of intermediate III (0.19 g) in THF (4.4 mL) at rt, in a microwave reactor vial. The vial was sealed, and the mixture was stirred at 110° C. for 5 min under microwave irradiation. The reaction mixture was cooled on an ice/water-bath and LAH (2 mL, 1M in THF) was added drop-wise. The resulting transparent solution was stirred at 80° C. for 10 min under microwave irradiation and then poured into ice-water (20 mL) and extracted with Et$_2$O (2×40 mL). The combined organic layers were washed with brine, dried (MgSO$_4$) and concentrated in vacuo. The crude intermediate was purified by silica gel chromatography (MeOH/EtOAc/Et$_3$N) to give 78 mg of an oil. This material was placed in a microwave reactor vial and 48% HBr (2 mL) was added. The vial was sealed, and the mixture was stirred at 150° C. for 0.5 h under microwave irradiation. The reaction vessel was cooled to rt and a brown solid precipitated. The crude product was suspended in EtOH (1 mL) in a microwave reactor vial. The reactor was sealed, and the mixture was stirred at 90° C. for 5 min under microwave irradiation. The vial was stored at 4° C. overnight, and the precipitated material was isolated by filtration and dried in vacuo. Yield of example 2c1: 51 mg as a solid. LC/MS (method 14): RT 0.56 min, ELSD 98.6%, UV 97.6%, MH$^+$: 248.2.

2c2 (4aS,10aS)-1-Ethyl-1,2,3,4,4a,5,10,10a-octahydro-benzo[g]quinoline-6,7-diol hydrobromide

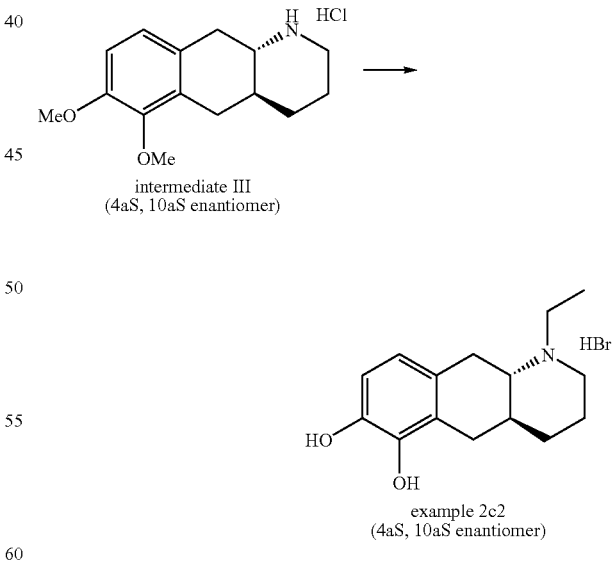

The procedure described for example 2c1 was followed using the enantiomeric starting material intermediate III (284 mg). Yield of example 2c2: 122 mg as a solid. LC/MS (method 14): RT 0.56 min, ELSD 98.9%, UV 97.4%, MH$^+$: 247.1.

2d1 (4aR,10aR)-1-n-Propyl-1,2,3,4,4a,5,10,10a-octahydro-benzo[g]quinoline-6,7-diol hydrobromide

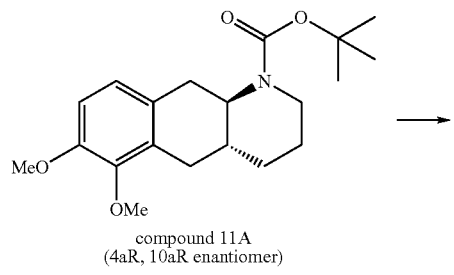

compound 11A
(4aR, 10aR enantiomer)

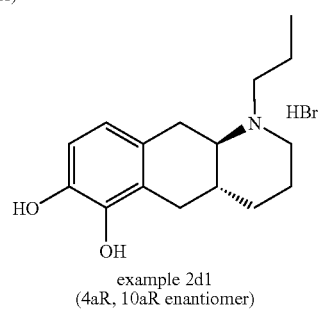

example 2d1
(4aR, 10aR enantiomer)

Compound 11A (0.5 g) was dissolved in 99% EtOH (5 mL) and treated with 2M HCl in Et$_2$O (4 mL) overnight at rt. The crude mixture was concentrated in vacuo, and the residue was partitioned between EtOAc and 10% aqueous NaOH (5 mL). The aqueous layer was extracted with EtOAc, and the combined organic layers were washed with brine, dried (MgSO$_4$), concentrated in vacuo. The residue was dissolved in 99% EtOH (5 mL) and treated with propionic aldehyde (0.52 mL), NaCNBH$_3$ (0.45 g), and AcOH (3 drops) overnight at rt. The crude mixture was portioned between sat. aqueous NaHCO$_3$ (12.5 mL), water (12.5 mL), and EtOAc (2×25 mL). The combined organic layers were washed with brine, dried (MgSO$_4$), and concentrated in vacuo. The residue was purified by silica gel chromatography (MeOH/EtOAc). The obtained intermediate was treated with 48% HBr (3 mL) at 150° C. for 1 h under microwave conditions, before the crude mixture was stored at 4° C. overnight. The precipitated material was isolated by filtration and dried in vacuo. Yield of example 2d1: 103 mg as a solid. LC/MS (method 25): RT 0.77 min, ELSD 99.1%, UV 95.3%, MH$^+$: 262.3.

2d2 (4aS,10aS)-1-n-Propyl-1,2,3,4,4a,5,10,10a-octahydro-benzo[g]quinoline-6,7-diol hydrobromide

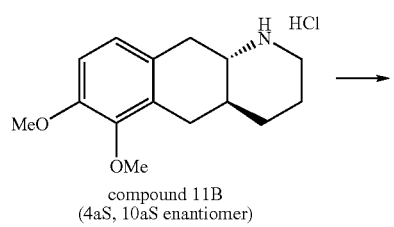

compound 11B
(4aS, 10aS enantiomer)

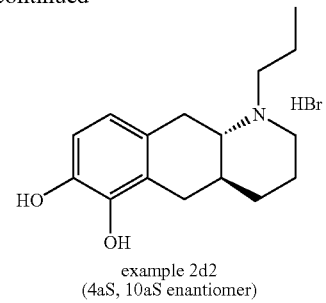

example 2d2
(4aS, 10aS enantiomer)

The procedure described for example 2d1 was followed starting from compound 11B (0.5 g). Yield of example 2d2: 70 mg as a solid. LC/MS (method 25): RT 0.70 min, ELSD 99.0%, UV 94.1%, MH$^+$: 262.1.

A small sample of example 2d2 was dissolved in MeOH and allowed to crystallize slowly at rt over 2 months. The formed white crystals were collected and subjected to X-ray analysis (cf. FIG. 2).

2e1 (4aR,10aR)-1-(2-Hydroxy-ethyl)-1,2,3,4,4a,5,10,10a-octahydro-benzo[g]quinoline-6,7-diol trifluoroacetate intermediate II
(4aR, 10aR enantiomer)

example 2e1
(4aR, 10aR enantiomer)

Et$_3$N (0.05 mL), and methoxyacetyl chloride (4 drops) were added to a suspension intermediate II (28 mg) in THF (1.5 mL) at rt, in a microwave reactor vial. The vial was sealed, and the mixture was stirred at 110° C. for 5 min under microwave irradiation. The reaction mixture was cooled to rt, and LAH (0.25 mL, 1M in THF) was added drop-wise. The crude mixture was stored at rt overnight and then poured into water (2 mL) and extracted with Et$_2$O (2×5 mL). The combined organic extracts were purified by silica gel chromatography (MeOH/EtOAc/Et$_3$N) to give 11 mg of an oil. This material was placed in a microwave reactor vial and 48% HBr (0.5 mL) was added. The vial was sealed, and the mixture was stirred at 150° C. for 0.5 h under microwave irradiation. The crude mixture was concentrated in vacuo, and the residue was purified by preparative LC/MS. Yield of example 2e1: 3.4 mg as oil. LC/MS (method 314): RT 0.45 min, ELSD 99%, very weak UV-signal at 254 nm, MH+: 263.8.

2f1 (4aR,10aR)-1-Allyl-1,2,3,4,4a,5,10,10a-octahydro-benzo[g]quinoline-6,7-diol hydrobromide

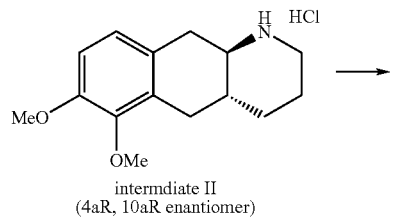
intermdiate II
(4aR, 10aR enantiomer)

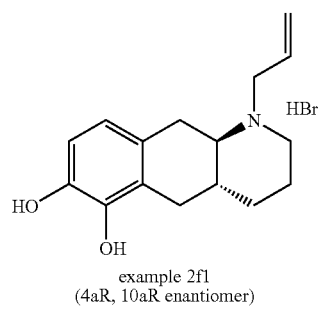
example 2f1
(4aR, 10aR enantiomer)

K$_2$CO$_3$ (0.17 g) and allyl bromide (0.09 mL) were added to a stirred solution of intermediate II (0.20 g) in DMF (7 mL) at rt. The suspension was stirred at rt for 1 h, and then poured into water (10 mL) and extracted with EtOAc (3×15 mL). The combined organic extracts were washed with brine, dried (Na$_2$SO$_4$), filtered and concentrated in vacuo. The crude intermediate was purified by silica gel chromatography (MeOH/EtOAc/Et$_3$N). Yield: 156 mg as a transparent oil. This material was dissolved in DCM (3.5 mL) and BBr$_3$ (0.9 mL, 1M in DCM) was added drop-wise at −78° C. The reaction mixture was stirred at rt for 1 h, and then quenched at −78° C. by slow addition of MeOH (10 mL). The reaction mixture was stirred at rt for 5 min, after which Et$_2$O (10 mL) was added. The reaction flask was stored at 4° C. for 1 h, and the precipitated product isolated by filtration and dried in vacuo. Yield of example 2f1: 50 mg as a white solid. LC/MS (method 25): RT 0.72 min, ELSD 99.7%, UV 100%, MH+: 260.3.

2g1 (4aR,10aR)-1-Prop-2-ynyl-1,2,3,4,4a,5,10,10a-octahydro-benzo[g]quinoline-6,7-diol

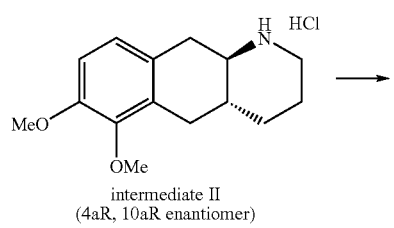
intermediate II
(4aR, 10aR enantiomer)

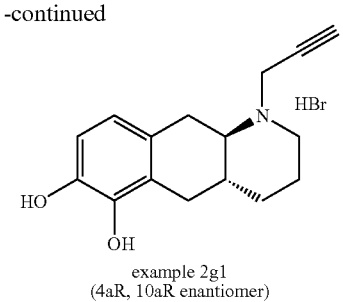
example 2g1
(4aR, 10aR enantiomer)

K$_2$CO$_3$ (105 mg) and propargyl chloride (45 mg) were added to a stirred solution of intermediate II (142 mg) in DMF (5 mL) at rt. The suspension was stirred at rt overnight, and then poured into water (20 mL) and extracted with EtOAc (2×30 mL). The combined organic extracts were washed twice with brine, dried (Na$_2$SO$_4$) and concentrated in vacuo. The crude intermediate was purified by silica gel chromatography (MeOH/EtOAc/Et$_3$N) to afford a transparent oil. This material was dissolved in DCM (3 mL) and BBr$_3$ (0.8 mL, 1M in DCM) was added drop-wise at −78° C. The reaction mixture was stirred at rt for 1 h, and then quenched at −78° C. by slow addition of MeOH (1.5 mL). The reaction mixture was stirred at rt for 10 min, before it was concentrated in vacuo. The crude product was purified by precipitation from MeOH/Et$_2$O. Yield of example 2g1: 25 mg as a white solid. LC/MS (method 25): RT 0.69 min, ELSD 99.3%, UV 100%, MH+: 258.3.

2h1 (4aR,10aR)-1-cyclo-Propyl-1,2,3,4,4a,5,10,10a-octahydro-benzo[g]quinoline-6,7-diol hydrobromide

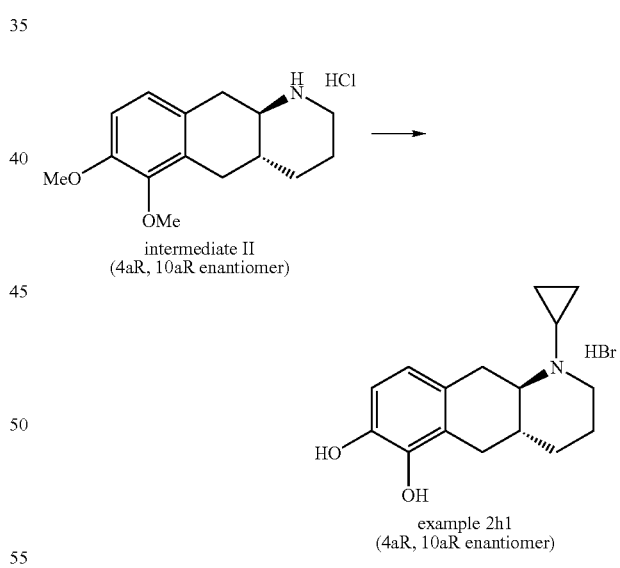
intermediate II
(4aR, 10aR enantiomer)

example 2h1
(4aR, 10aR enantiomer)

(1-Ethoxycyclopropoxy)trimethylsilane (1.05 mL) was added to a stirred solution of intermediate II (250 mg), NaCNBH$_3$ (276 mg) in MeOH (2.5 mL) and AcOH (0.5 mL). The vial was closed with a septum, and the mixture was stirred at 75° C. for 12 h. The crude mixture was filtered, and the filtrate was concentrated in vacuo. The crude product was dissolved in EtOAc and purified by silica gel chromatography (EtOAc) to afford an oil. This material was further purified by dissolving it in EtOAc and extraction with 0.5% HCl. The aqueous layer was basified and then extracted with EtOAc (2×25 mL). The combined organic layers were dried (Na$_2$SO$_4$) and concentrated in vacuo. The residue was suspended in 48% HBr (1.5 mL), and heated to 150° C. for 45 min in a sealed microwave reactor vial under microwave irradiation. The precipitated material was isolated by filtration and dried in vacuo. Yield of example 2h1: 91 mg as an off-white solid. LC/MS (method 102): RT 0.60 min, ELSD 99.2%, UV 96.5%, MH+: 260.0.

2i1 (4aR,10aR)-1-cyclo-butyl-1,2,3,4,4a,5,10,10a-octahydro-benzo[g]quinoline-6,7-diol hydrobromide

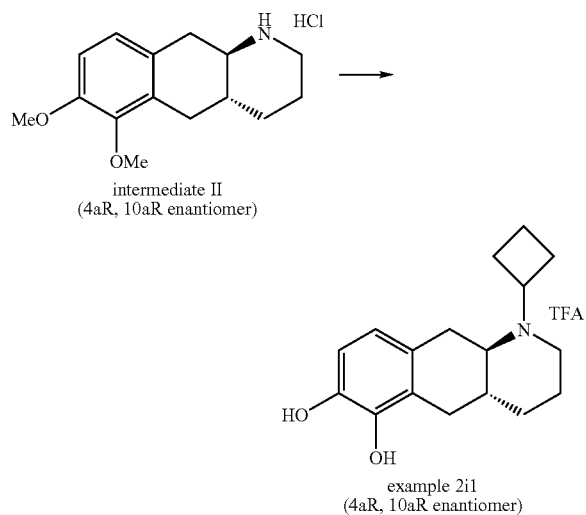

intermediate II
(4aR, 10aR enantiomer)

example 2i1
(4aR, 10aR enantiomer)

Intermediate II (250 mg) was dissolved in 1,2-dichloroenthane. NaCNBH₃ (280 mg) and cyclobutanone (0.32 mL) were added and the mixture was stirred at rt overnight. Then more NaCNBH₃ (60 mg) was added, and the mixture was stirred at rt over the weekend. The reaction was quenched with water and. The aqueous layer was extracted with 1,2-dichloroethane, and the combined organic layers were washed with brine, dried (MgSO₄), and concentrated in vacuo. The crude residue was purified by silica gel chromatography (EtOAc/MeOH/Et₃N) to afford an oil (160 mg). 122 mg of this material was dissolved in 48% HBr (3 mL) and heated to 150° C. for 15 min under microwave irradiation in a sealed vial. The precipitated material was collected by filtration, dried in vacuo. The residue was subjected to preparative LC/MS-purification. Yield of example 2i1: 13.3 mg as a solid. LC/MS (method 102): RT 0.73 min, ELSD 100%, UV 76.4%, MH+: 274.0.

3a1 (6aR,10aR)-6,6a,7,8,9,10,10a,11-Octahydro-1,3-dioxa-7-aza-cyclopenta[a]anthracene hydrochloride

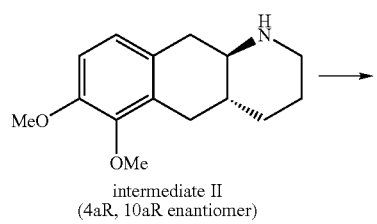

intermediate II
(4aR, 10aR enantiomer)

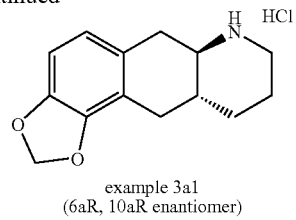

example 3a1
(6aR, 10aR enantiomer)

Intermediate II (567 mg) was treated with benzyl bromide (0.36 mL) and K₂CO₃ (472 mg) in dry DMF (20 mL) for 0.75 h. The crude mixture was poured into water (20 mL), and the intermediate was extracted into EtOAc (3×30 mL). The combined organic extracts were washed with brine, dried (Na₂SO₄), and concentrated in vacuo. The residue was purified by silica gel chromatography (EtOAc/heptane) to give a white solid (234 mg). 220 mg of this material was treated with 48% HBr (6.5 mL) at 160° C. for 0.5 h under microwave conditions. The precipitated intermediate was washed with MeOH and dried to give a white solid (180 mg). 160 mg of this material was treated with Cs₂CO₃ (326 mg), CH₂BrCl (49 microL) in DMF (2 mL) at 110° C. under microwave conditions for 0.5 h. More Cs₂CO₃ (300 mg) and CH₂BrCl (160 microL) were added, and the mixture was heated to 120° C. for 0.5 h under microwave conditions. The crude mixture was diluted with EtOAc (20 mL) and washed with brine (2×20 mL), dried (Na₂SO₄), and concentrated in vacuo. The residue was purified by silica gel chromatography (EtOAc/heptane) to give a solid (94 mg). This material was treated with 10% Pd/C (~50 mg), five drops of 37% HCl, and hydrogen gas (3 bar) in MeOH (20 mL) for 2 h. The catalyst was filtered off, and the filtrate was concentrated in vacuo. The resulting solid was dried in vacuo to give example 3a1 as a white solid (79 mg). LC/MS (method 25): rt 0.90 min, ELSD 99.8%, UV 95.6%. MH+: 232.1.

3b1 (6aR,10aR)-7-Methyl-6,6a,7,8,9,10,10a,11-octahydro-1,3-dioxa-7-azacyclopenta[a]anthracene

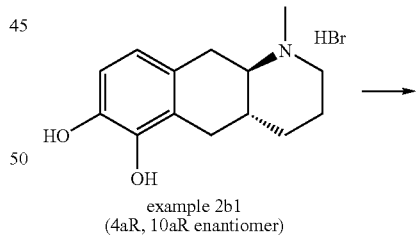

example 2b1
(4aR, 10aR enantiomer)

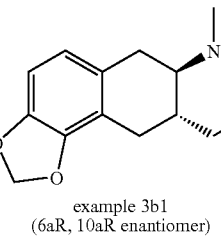

example 3b1
(6aR, 10aR enantiomer)

Example 2b1 (700 mg), Cs₂CO₃ (1.7 g), CH₂BrCl (0.22 mL) and DMF (5 mL) were heated to 110° C. for 0.5 h in a sealed microwave reactor vial under microwave irradiation. The crude mixture was purified by passing it through a plug of silica gel (MeOH/DCM). Yield of example 3b1: 7 mg as a solid. LC/MS (method 23 SUN): RT 0.62 min. ELSD 99.0%. UV 80.7%. MH⁺: 246.3.

3c1 (6aR,10aR)-7-Ethyl-6,6a,7,8,9,10,10a,11-octahydro-1,3-dioxa-7-aza-cyclopenta[a]anthracene hydrochloride

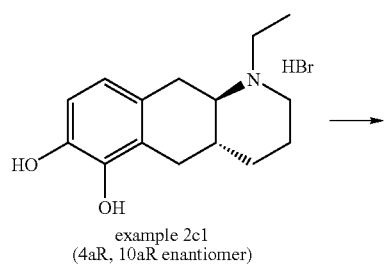

example 2c1
(4aR, 10aR enantiomer)

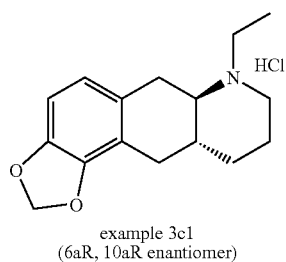

example 3c1
(6aR, 10aR enantiomer)

Example 2c1 (475 mg), Cs₂CO₃ (1.2 g), CH₂BrCl (0.15 mL), and DMF (5 mL) were heated to 110° C. for 0.5 h in a sealed microwave reactor vial under microwave irradiation. The crude mixture was purified by passing it through a plug of silica gel (MeOH/DCM). The isolated material was dissolved in MeOH and 2 M HCl in Et₂O was added followed by Et₂O. The precipitated product was isolated by filtration and dried in vacuo. Yield of example 3c1: 15 mg as a solid. LC/MS (method 23). RT 0.87 min. ELSD 94.8%. UV 90.9%. MH⁺: 260.0.

3d1 (6aR,10aR)-7-n-Propyl-6,6a,7,8,9,10,10a,11-octahydro-1,3-dioxa-7-aza-cyclopenta[a]anthracene hydrochloride

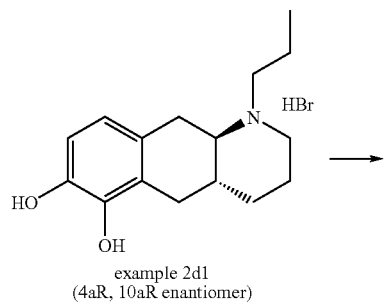

example 2d1
(4aR, 10aR enantiomer)

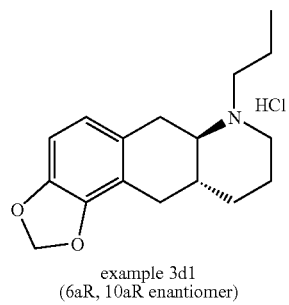

example 3d1
(6aR, 10aR enantiomer)

Example 2d1 (7.80 g), Cs₂CO₃ (18.6 g), CH₂BrCl (2.2 mL), and DMF (180 mL) were heated to 100° C. for 1 h under an argon atmosphere. The crude reaction mixture was added to separatory funnel and diluted with ice/water (300 mL). The resulting mixture was extracted with Et₂O (3×300 mL). The combined organic layers were washed with brine (200 mL), dried (MgSO₄) and concentrated in vacuo. The residue was purified by silica gel chromatography (EtOAc/MeOH) to afford a pale red solid, which was dissolved in MeOH (25 mL) and precipitated as the hydrochloride salt by addition of 2 M HCl in Et₂O (20 mL) and Et₂O (100 mL). The precipitated product was isolated by filtration and dried in vacuo. Yield of example 3d1: 5.1 g. LC/MS (method 111): RT 0.70 min. ELSD 100%. UV 97.0%. MH⁺: 274.0.

4a1 Acetic acid (4aR,10aR)-7-acetoxy-1,2,3,4,4a,5,10,10a-octahydro-benzo[g]quinolin-6-yl ester trifluoroacetate

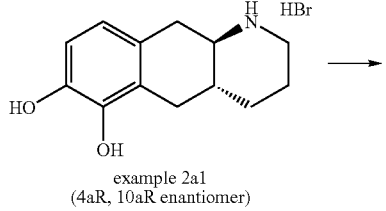

example 2a1
(4aR, 10aR enantiomer)

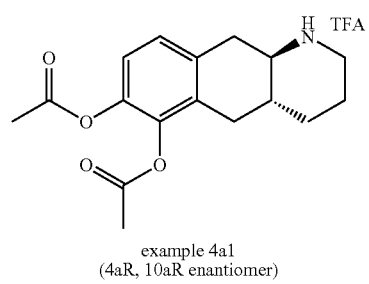

example 4a1
(4aR, 10aR enantiomer)

AcCl was added to a stirred suspension of example 2a1 (90 mg) in DCM (1 mL) and TFA (3 mL). The solution was stirred at rt for 2.5 h. before it was concentrated in vacuo. The residue was subjected to preparative LC/MS-purification. Fractions containing example 4a1 were pooled and the acetonitrile was removed by concentration in vacuo. The residual aqueous solution was lyophilized in vacuo. Yield of example 4a1: 49 mg as a white solid. LC/MS (method 14): RT 1.33 min, ELSD 99.5%, UV 98.7%. MH+: 304.0.

4a2 Acetic acid (4aR,10aR)-7-acetoxy-1,2,3,4,4a,5,10,10a-octahydro-benzo[g]quinolin-6-yl ester trifluoroacetate

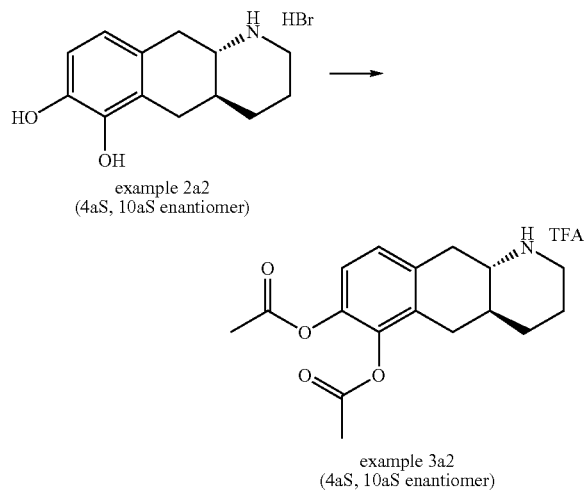

example 2a2
(4aS, 10aS enantiomer)

example 3a2
(4aS, 10aS enantiomer)

The procedure described for example 4a1 was followed starting from example 2a2 (30 mg). Yield of example 4a2: 21 mg as a white solid. LC/MS (method 14): RT 1.33 min, ELSD 99.5%, UV 98.5. MH+: 304.0.

4b1 2,2-Dimethyl-propionic acid (4aR,10aR)-7-(2,2-dimethyl-propionyloxy)-1-methyl-1,2,3,4,4a,5,10,10a-octahydro-benzo[g]quinolin-6-yl ester trifluoroacetate

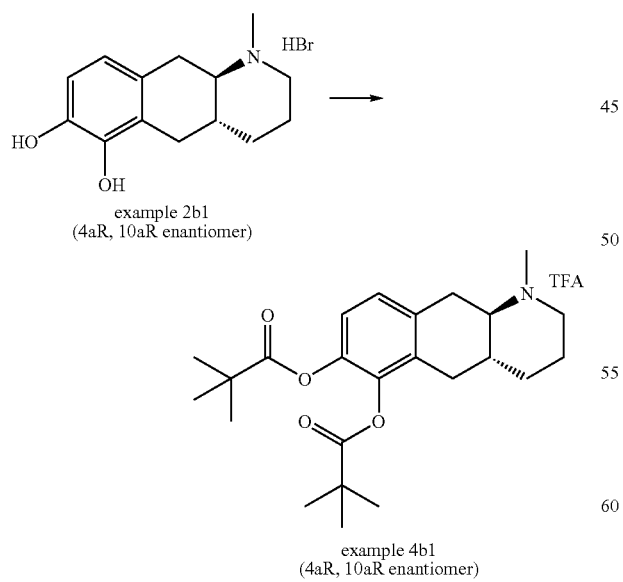

example 2b1
(4aR, 10aR enantiomer)

example 4b1
(4aR, 10aR enantiomer)

PivCl (0.064 mL) was added to a stirred solution of example 2b1 (41 mg) in TFA (0.7 mL) at 0° C. The solution was stirred at 0° C. for 5 min after which more PivCl (0.128 mL) was added. The solution was stirred at rt for 2 h, before it was concentrated in vacuo and the residue was subjected to preparative LC/MS-purification. Fractions containing example 4b1 were pooled, the acetonitrile was removed by concentration in vacuo, and the aqueous residue was lyophilized in vacuo to give the product. Yield of example 4b1: 7 mg as a white solid. LC/MS (method 14): RT 2.27 min, ELSD 99.6%, UV 77.6%. MH+: 401.2.

4b2 Acetic acid (4aS,10aS)-6-acetoxy-1-methyl-1,2,3,4,4a,5,10,10a-octahydro-benzo[g]quinolin-7-yl ester trifluoroacetate

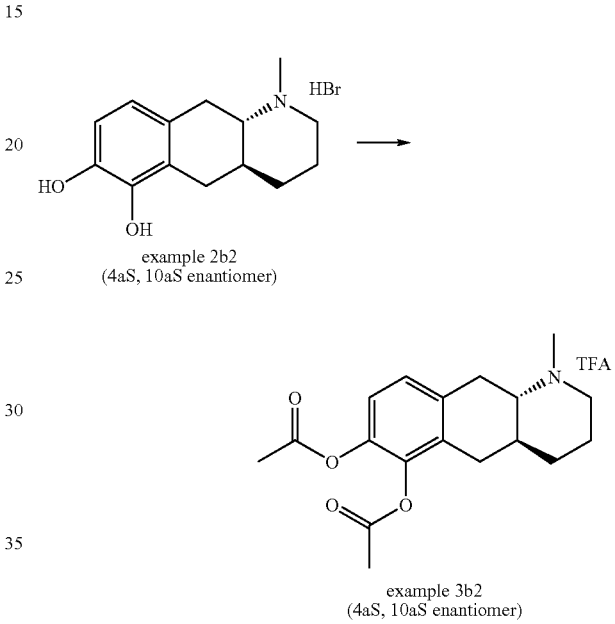

example 2b2
(4aS, 10aS enantiomer)

example 3b2
(4aS, 10aS enantiomer)

Example 2b2 (18 mg) was treated with AcCl (56 micro-L) in TFA (0.5 mL) at rt for ~1 h. The crude mixture was concentrated in vacuo. The residue was purified by preparative LC/MS. Fractions containing example 4b2 were pooled, the acetonitrile was removed by concentration in vacuo, and the aqueous residue was lyophilized in vacuo to give the product. Yield of example 4b2: 6 mg as a white solid. LC/MS (method 14): RT 1.33 min, ELSD 99.8%, UV 93.7%. MH+: 318.0.

4c2 Acetic acid (4aS,10aS)-6-acetoxy-1-ethyl-1,2,3,4,4a,5,10,10a-octahydro-benzo[g]quinolin-7-yl ester trifluoroacetate

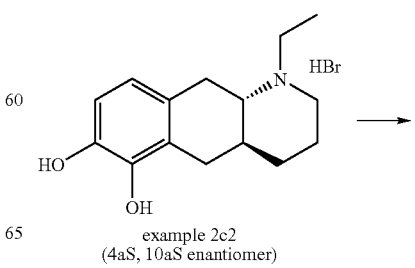

example 2c2
(4aS, 10aS enantiomer)

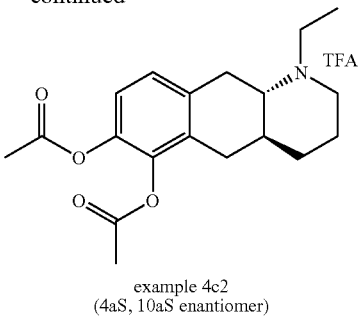

example 4c2
(4aS, 10aS enantiomer)

Prepared as example 4b1 from example 2c2 (32 mg). Yield of example 4c2: 7 mg as a solid. LC/MS (method 14): RT 1.41 min, ELSD 98.6%, UV 53.2%. MH⁺: 332.2.

4d1 2,2-Dimethyl-propionic acid (4aR,10aR)-7-(2,2-dimethyl-propionyloxy)-1-n-propyl-1,2,3,4,4a,5,10,10a-octahydro-benzo[g]quinolin-6-yl ester trifluoroacetate

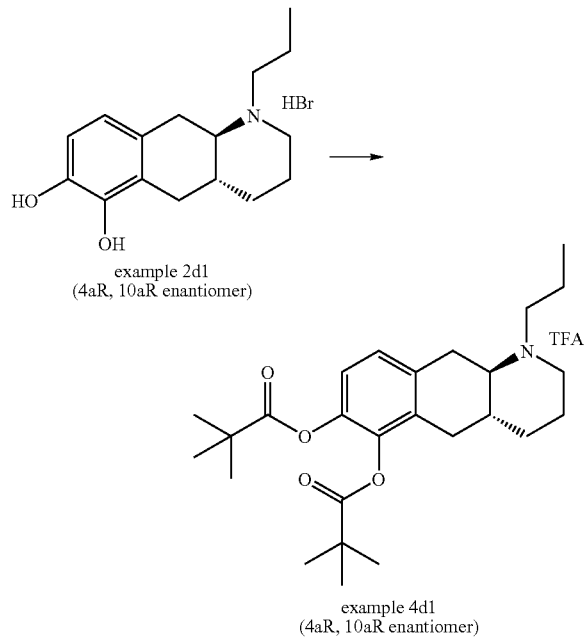

example 2d1
(4aR, 10aR enantiomer)

example 4d1
(4aR, 10aR enantiomer)

Example 4d1 was prepared in a similar manner as example 4b1 starting from example 2d1 (44 mg). Yield of example 4d1: 14 mg as a white solid. LC/MS (method 14): RT 2.45 min, ELSD 97.7%, UV 83.9%. MH⁺: 430.2.

5d1 Racemic cis-7-Propyl-6,6a,7,8,9,10,10a,11-octahydro-1,3-dioxa-7-aza-cyclopenta[a]anthracene

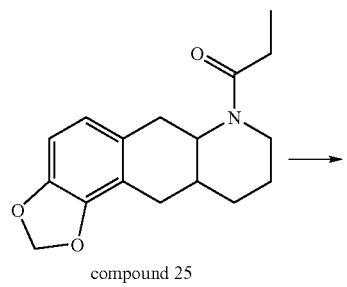

compound 25

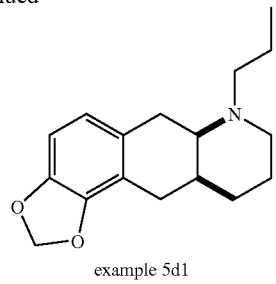

example 5d1

Compound 25 (0.34 g dissolved in THF (5 mL)) was added to a suspension of LAH (0.3 g) in THF (5 mL) at 0° C. The mixture was stirred at for 40 min, before it was quenched with ice/water and basified with 27% aqueous NaOH. The product was extracted into 2-methyl-THF. The organic layer was washed with sat. aqueous NaHCO₃, dried (MgSO₄), and concentrated in vacuo. The residue was dissolved in MeOH (3 mL) and treated with a few mg of 5% Pd/C, 37% aqueous HCl (10 drops), and hydrogen gas (3 bar) at 50° C. for ~1 h and further at rt (1 bar hydrogen pressure) overnight. Next morning, a few mg of additional 5% Pd/C were added, and the mixture was hydrogenated (3 bar) at 50° C. overnight (this procedure was repeated several times over a total of four days). The catalyst was filtered off, and the filtrate was concentrated in vacuo. The residue was partitioned between 2M aqueous NaOH and DCM. The organic layer was washed with sat. aqueous NaHCO₃, dried (MgSO₄), and diluted with 2M HCl in Et₂O and concentrated in vacuo. The residue was dissolved in MeOH, and treated with 2M HCl in Et₂O at 0° C. The precipitated product was isolated by filtration. Yield of example 5d1: 53 mg as a white solid. LC/MS (method 111): RT 0.71 min, ELSD 100%, UV 61%. MH⁺: 274.1.

Abbreviations and List of Chemicals Used

The following abbreviations are used. This paragraph also outlines the chemicals used along with their commercial source (not included for standard solvents).

AcCl=acetyl chloride (e.g. Aldrich 23,957-7). ACh=acetylcholine. AcOH=acetic acid. AD=Alzheimer's disease. ADME=absorption-distribution-metabolism-excretion. Allyl bromide (e.g. Fluka 05870) AlCl₃=aluminium chloride (e.g. Aldrich 29,471-3). α$_D$=specific optical rotation. BBr₃=boron tribromide (used as DCM solution; Aldrich 17,893-4). Boc₂O=Boc anhydride/di-t-butyl dicarbonate (e.g. Aldrich 19,913-3). Brine=saturated aqueous solution of sodium chloride. BSA=bovine serum albumin. (s-Butyl) lithium (used as a cyclo-hexane solution; e.g. Aldrich 19,559-6). cAMP=cyclic adenosine monophosphate. Celite=filter-aid. CH₂BrCl=bromochloromethane (Aldrich 13,526-7). CH₃I=methyl iodide/iodomethane (e.g. Aldrich 28,956-6). CHO cell=Chinese hamster ovary cell. ClAcCl=chloroacetyl chloride (e.g. Aldrich 10,449-3). Cs₂CO₃=cesium carbonate (Aldrich 441902). CuI=copper(I) iodide (Aldrich 215554). Cyclobutanone (e.g. Aldrich C9,600-1). cyclo-propyl methyl bromide/(bromomethyl)-cyclo-propane (Aldrich 24,240-3). DA=dopamine. D1=dopamine D1 receptor. D2=dopamine D2 receptor. D3=dopamine D3 receptor. D4=dopamine D4 receptor. D5=dopamine D5 receptor. DCM=dichloromethane/methylene chloride. 1,6-dibromo-2-naphthol (e.g. Aldrich D4,180-5). DMF=dimethyl formamide. DMSO=dimethyl sulfoxide. L-DOPA=(levo)-3,4-dihydroxy phenylalanine. DOPAC=3,4-dihydroxyphenyl acetic acid (DA metabolite). EC₅₀=concentration required to induce a response halfway between the baseline and the maximum response for the compound in question. ELSD=evaporative light scattering detection. Et$_3$N=triethyl amine. Et$_2$NH=diethyl amine. EtOAc=ethyl acetate. Ethyl 2-chloro-nicotinate (e.g. ABCR AV20359). 99% EtOH=absolute ethanol. Ethyl magnesium bromide (used as a 3 M solution in Et$_2$O; Aldrich 18,987-1). Et$_2$O=diethyl ether. [(1-Ethoxycyclopropyl)-oxy]trimethyl-silane (Aldrich 332739). Ethylene glycol=1,2-ethanediol. 35% H$_2$O$_2$=35% aqueous solution of hydrogen peroxide (e.g. Aldrich 34,988-7). FLIPR=fluorometric imaging plate reader. FSB=foetal bovine serum. h=hours. 48% HBr=48% aqueous solution of hydrogen bromide. 18%/37% HCl=18%/37% aqueous solution of hydrogen chloride. 1 M HCl/2 M HCl=1 M/2 M aqueous solution of hydrogen chloride (unless noted specifically as a 2M Et$_2$O solution, which is commercially available, e.g. Aldrich 45,518-0). HMPA=hexamethylphosphorous triamide. HVA=homovanillic acid (DA metabolite). i=iso. IBMX=3-i-butyl-1-methylxanthine. i.d.=inner diameter. 1-Iodopropane (e.g. Aldrich 17,188-3). K$_2$CO$_3$=potassium carbonate (e.g. Aldrich 20,961-9). KMnO$_4$=potassium permanganate (e.g. Aldrich 39,912-4). KO=knock-out. LDA=lithium di-i-propylamide (used as a THF/heptane/ethylbenzene solution; Fluka 62491). LC/MS=high-performance liquid chromatography/mass spectrometer. LAH=lithium aluminium hydride (used as a 1M THF solution; Aldrich 21,277-6). LiCl=lithium chloride (e.g. Aldrich 31,046-8). L-Selectride=lithium tri-s-butylborohydride (used as a 1M THF solution; Aldrich 17,849-7). MDO=methylene-di-oxy. MED=minimal effective dose. MED$_{Nemonapride}$=minimal effective dose in the presence of Nemonapride. MeOH=methanol. methoxyacetyl chloride (e.g. Aldrich M965-3). min=minutes. MBD=minimal brain dysfunction. 2-Methyl-THF (e.g. Aldrich 41,424-7). MPTP=1-methyl-4-phenyl-1,2,3,6-tetrahydropyridine. MTBE=methyl t-butyl ether. n=normal. NaCNBH$_3$=sodium cyanoborohydride (Aldrich 15,615-9). Na$_2$S$_2$O$_3$=Sodium bisulfite (used as an 38-40% aqueous solution; eg. Riedel 13438). NaH=sodium hydride (used as a 60% dispersion; Aldrich 45,291-2). NaIO$_4$=sodium periodate (e.g. Aldrich 31,144-8). 1 M/9 M NaOH=1 M/9 M aqueous solution of sodium hydroxide. NaOMe=sodium methoxide (used as a ca. 5 M solution in methanol; e.g. Aldrich 15,625-6). NPA=N-n-propyl Apomorphine. 6-OHDA=6-hydroxydopamine. PBS=phosphate buffered saline (0.02 M sodium phosphate buffer with 0.15 M sodium chloride, pH adjusted to 7.4). PD=Parkinson's disease. PFC=prefrontal cortex. Pd/C=palladium-on-charcoal (e.g. Aldrich 20,569-9). Pd(OAc)$_2$=palladium(II)acetate (Alfa Aesar 010516). Piperonyl alcohol (e.g. Aldrich P4,940-6). PK=pharmaco-kinetic. PLMD=periodic limb movement disorder. Propargyl chloride (e.g. Aldrich 14,399-5). Propionaldehyde (e.g. Aldrich 58,812-4). PTSA=para-toluene sulfonic acid hydrate (e.g. Aldrich 40,288-5). PivCl=pivaloyl chloride/trimethyl acetyl chloride (e.g. Aldrich T7,260-5). RLS=restless legs syndrome. rt=room temperature. RT=retention time. s=secondary. sat. NaHCO$_3$=saturated aqueous solution of sodium hydrogen carbonate. sat. NH$_4$Cl=saturated aqueous solution of ammonium chloride. SC=subcutaneous. SFC=supercritical flash chromatography. Sodium metal (e.g. Aldrich 28,205-7). t=tertiary. TBAI=tetra-n-butyl ammonium iodide (e.g. Aldrich 14,077-5). TFA=trifluoroacetic acid. TFAA=trifluoroacetic acid anhydride. THF=tetrahydrofuran (dried over 4 Å molecular sieves). TLC=thin layer chromatography. CH(OCH$_3$)$_3$=trimethyl orthoformate (e.g. Aldrich 30,547-2). UV=ultraviolet purity (at 254 nm unless noted differently).

Pharmacological Testing

D1 cAMP Assay

The ability of the compounds to either stimulate or inhibit the D1 receptor mediated cAMP formation in CHO cells stably expressing the human recombinant D1 receptor was measured as follows. Cells were seeded in 96-well plates at a concentration of 11000 cells/well 3 days prior to the experiment. On the day of the experiment the cells were washed once in preheated G buffer (1 mM MgCl$_2$, 0.9 mM CaCl$_2$, 1 mM IBMX (3-i-butyl-1-methylxanthine) in PBS (phosphate buffered saline)) and the assay was initiated by addition of 100 micro-L of a mixture of 30 nM A68930 and test compound diluted in G buffer (antagonism) or test compound diluted in G buffer (agonism).

The cells were incubated for 20 minutes at 37° C. and the reaction was stopped by the addition of 100 micro-L S buffer (0.1 M HCl and 0.1 mM CaCl$_2$) and the plates were placed at 4° C. for 1 h. 68 micro-L N buffer (0.15 M NaOH and 60 mM NaOAc) was added and the plates were shaken for 10 minutes. 60 micro-l of the reaction were transferred to cAMP FlashPlates (DuPont NEN) containing 40 micro-L 60 mM Sodium acetate pH 6.2 and 100 micro-L IC mix (50 mM Sodium acetate pH 6.2, 0.1% sodium azide, 12 mM CaCl$_2$, 1% BSA (bovine serum albumin) and 0.15 micro-Ci/mL $^{125}$I-cAMP) were added. Following an 18 h incubation at 4° C. the plates were washed once and counted in a Wallac TriLux counter.

D2 cAMP Assay

The ability of the compounds to either stimulate or inhibit the D2 receptor mediated inhibition of cAMP formation in CHO cells transfected with the human D2 receptor was measure as follows. Cells were seeded in 96 well plates at a concentration of 8000 cells/well 3 days prior to the experiment. On the day of the experiment the cells were washed once in preheated G buffer (1 mM MgCl$_2$, 0.9 mM CaCl$_2$, 1 mM IBMX in PBS) and the assay was initiated by addition of 100 micro-l of a mixture of 1 micro-M quinpirole, 10 microM forskolin and test compound in G buffer (antagonism) or 10 micro-M forskolin and test compound in G buffer (agonism).

The cells were incubated 20 minutes at 37° C. and the reaction was stopped by the addition of 100 micro-l S buffer (0.1 M HCl and 0.1 mM CaCl$_2$) and the plates were placed at 4° C. for 1 h. 68 micro-L N buffer (0.15 M NaOH and 60 mM Sodium acetate) were added and the plates were shaken for 10 minutes. 60 micro-L of the reaction were transferred to cAMP FlashPlates (DuPont NEN) containing 40 micro-L 60 mM NaOAc pH 6.2 and 100 micro-L IC mix (50 mM NaOAc pH 6.2, 0.1% Sodium azide, 12 mM CaCl$_2$, 1% BSA and 0.15 micro-Ci/ml $^{125}$I-cAMP) were added. Following an 18 h incubation at 4° C. the plates were washed once and counted in a Wallac TriLux counter.

D5 Assay

Concentration-dependent stimulation of intracellular Ca$^{2+}$ release by dopamine in hD5-transfected CHO-Ga16 cells. The cells were loaded with fluoro-4, a calcium indicator dye, for 1 h. Calcium response (fluorescence change) was monitored by FLIPR (fluorometric imaging plate reader) for 2.5 min. Peak responses (EC$_{50}$) were averaged from duplicate wells for each data point and plotted with drug concentrations (cf. FIG. 1 for dopamine).

Concentration effects curves to agonists were constructed by adding different concentrations to different wells using a Fluorescence Imaging Plate Reader (FLIPR™) (Molecular Devices, Sunnyvale, Calif.). Curves were fitted with sigmoidal dose response equation I=I$_{max}$/(1+(EC$_{50}$/[Agonist])$^n$), where the EC$_{50}$ value is the concentration of agonist that produced half-maximal activation, and n is the Hill coefficient. Fits were made using the Graphpad Prism 4 software (San Diego, Calif.).

D1/D2 Dissections

Dopamine agonists can have activity at either the D1-like receptors, the D2-like receptors, or both. We have used the rotation response in rats with unilateral 6-OHDA lesions to assess compounds for their ability to stimulate both receptor types and induce rotation [Ungerstedt, Arbuthnott; Brain Res., 24, 485 (1970); Setler, Sarau, Zirkle, Saunders; Eur. J. Pharmacol., 50(4), 419 (1978); Ungerstedt, Herrera-Marschitz, Jungnelius, Ståhle, Tossman, Zetterström; in "Advances in Dopamine Research" (Kohsaka, Ed.), Pergamon Press, Oxford, p. 219 (1982)]. Experiments consist of determining a minimum effective dose (MED) to induce rotation for the compound in question. Once a MED has been determined, a second experiment is performed to determine the MED of the compound to overcome Nemonapride block ($MED_{Nemonapride}$). Nemonapride is a D2-like antagonist that blocks the D2-like receptor, therefore any observed rotations would be dependent upon activity at the D1-like receptor. Finally, once the $MED_{Nemonapride}$ is known a third experiment is run using the $MED_{Nemonapride}$ dose and observing the effect of the D1-like antagonist, SCH 23390 alone, the D2-like antagonist, Nemonapride alone and finally, the effect of combined treatment with SCH 23390 and Nemonapride. This third experiment confirms the activity of the compound at both receptors as either antagonist alone can only partially inhibit the rotation response induced by the test compound while the combination treatment completely blocks all rotations in the rats [Arnt, Hytell; Psychopharmacology, 85(3), 346 (1985); Sonsalla, Manzino, Heikkila; J. Pharmacol Exp. Ther., 247(1), 180 (1988)]. This model was validated using Apomorphine as the proof-of-principle compound for mixed D1-like/D2-like agonists.

Superiority Model

Apomorphine and L-DOPA are able to reverse motility deficits in a mouse model of severe dopamine depletion. Both Apomorphine and L-DOPA stimulate D1 and D2-like dopamine receptors. Pramipexole, an agonist at D2-like receptors is ineffective in this model. Some of the compounds included herein have been tested in this model and exhibit a profile similar to Apomorphine and L-DOPA in that they are able to restore locomotion in the mice. In this way, these compounds are 'superior' to other compounds, such as Pramipexole, that target D2-like receptors only.

Dyskinesia Model

The dyskinetic profile of some of the compounds of the invention was studied using an animal model described in the literature [Lundblad, Andersson, Winkler, Kirik, Wierup, Cenci; Eur. J. Neurosci., 15(1), 120 (2002)]. In this paradigm some of the compounds of the invention gave less dyskinesias than L-DOPA or Apomorhine in drug-naïve animals. Some of the compounds of the invention further reduced L-DOPA induced dyskinesias significantly more than was observed when shifting animals from L-DOPA to Pramipexole.

Methods—Cell Culture

Human D5 (hD5) expression construct was made using a modified pEXJ vector. A stable cell line expressing a promiscuous human Galpha16 G protein (CHO-Ga16) was purchased from (Molecular Devices, Sunnyvale, Calif.). The cells were cultured in HAMS F-12 media (Invitrogen, Carlsbad, Calif.) containing 10% FSB (foelal bovine serum), 1% L-glutamine and 1% penicillin/streptomycin (P/S) at 37° C. in 5% $CO_2$. 48 h before assay, CHO-Ga16 cells were transiently transfected with hD5 receptor DNA using a lipofectamine Plus method (Invitrogen, Carlsbad, Calif.), and allow to grow for 1 day in serum and P/S free media. 24 h before assay, hD5 transfected CHO-Ga16 cells were seeded at a density of 10,000 cells per well into black walled clear-base 384-well plates pretreated with poly-D-Lysine (Becton Dickinson, USA). The cells were then cultured in HAMS F-12 cell growth media containing 1.5% FBS, 1% L-glutamine and 1% penicillin/streptomycin (P/S) at 37° C. in 5% $CO_2$ Methods—Intracellular Calcium Mobilization Assays For measurements of intracellular free calcium concentration ($[Ca^{2+}]_i$), the culture medium was replaced with a freshly prepared loading buffer. The loading buffer contains 1× HBSS (Invitrogen), 20 mM HEPES (Sigma), 0.1% BSA (Sigma), 1.5 micro-M Fluoro-4-AM (Molecular Probes), and 2.5 mM probenecid (prepared fresh) (Sigma). The plates were incubated for 1 h at 37° C. and 5% $CO_2$ and washed three times with washing buffer. The washing buffer contains the same components as the loading buffer excluding Fluo-4-AM. The cells were then placed into a fluorescence imager plate reader (FLIPR™, Molecular Devices) to monitor cell fluorescence before and after addition of various compounds.

The compounds of interest were diluted in washing buffer to a 4× final concentration and aliquoted into a clear round-bottom plate. The dye was excited at the 488 nm wavelength using an argon ion laser and the signal was detected using the standard 510-570 nm emission [Sullivan, Tucker, Dale; Methods Mol. Biol., 114, 125 (1999)]. Concentration effects curves for agonists were constructed by adding different concentrations to different wells. Relative fluorescence is measured by subtracting basal from peak fluorescence after addition of drug. The data were then collected and analyzed using the FLIPR™ software and GraphPad Prism 4.

Antagonist activities of compounds were assayed for their inhibition of the signal elicited by agonist ligands. Cells were pre-incubated with compounds at increasing concentrations, and then stimulated with agonists using the methods described above.

In vitro Hepatocyte Assay

Cryopreserved pooled male rat hepatocytes (Sprague Dawley) and pooled human hepatocytes from 10 donors (male and female) were purchased from In Vitro Technologies Inc., BA, USA. Cells were thawed at 37° C. in a water bath, live cells counted and seeded in a total of 100 micro-L in Dulbecco's modified Eagle medium (high glucose) with 5 mM Hepes buffer in 96 well plates, each well containing 250.000 and 500.000 cells/mL for rat and human hepatocytes, respectively. Incubations were started after 15 min of pre-incubation and stopped at time points of 0, 5, 15, 30 and 60 min for rats and at 0, 30, 60, 90 and 120 min for human hepatocytes. Incubations were stopped by addition of an equal volumes of ice-cold acetonitrile containing 10% 1 M HCl. Following centrifugation, 20 micro-L of the supernatants were injected on a HPLC Column Atlantis dC18 3 micro-m, 150×2.1 mm i.d. (Waters, Mass., USA). The mobile phase had the following composition: A: 5% acetonitrile, 95% $H_2O$, 3.7 ml/l 25% aq. $NH_3$, 1.8 mL/L formic acid. Mobile phase B: 100% acetonitrile and 0.1% formic acid. The flow rate was 0.3 ml/min. The gradient operated from 0% to 75% B from 5 min to 20 min and the eluate was analyzed using a Q-TOFmicro mass spectrometer (Waters, Mass., USA). Formation of the product/metabolite was confirmed by accurate mass measurements and comparison with a synthesized standard giving coinciding retention times.

What is claimed:
1. A compound having the structure I

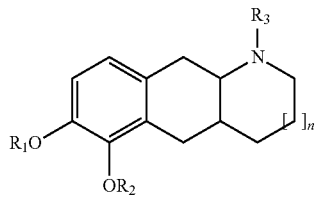

wherein n=1
wherein $R_1$ and $R_2$ are fused and form a methylene ($CH_2$) group, a carbonyl (C=O) group, or an oxalyl (O=C—C=O) group
$R_3$ is selected from the group consisting of hydrogen, methyl, ethyl, n-propyl, cyclo-propyl, cyclo-butyl, allyl, propargyl, hydroxyethyl, 3-fluoropropyl and 2-fluoroethyl,
and pharmaceutically acceptable acid addition salts thereof.

2. The compound according to claim 1 wherein $R_3$ is selected from the group consisting of hydrogen, methyl, ethyl, n-propyl, allyl, and propargyl.

3. The compound according to claim 1 wherein $R_3$ is selected from the group consisting of cyclo-propyl, cyclo-butyl, and hydroxyethyl.

4. The compound according to claim 1 further characterized by being the substantially pure trans-diastereoisomer.

5. The compound according to claim 1 wherein $R_1$ and $R_2$ are fused and form a methylene ($CH_2$) group.

6. The compound according to claim 1 wherein n=1, further characterized by being the substantially pure (6aR,10aR)-enantiomer.

7. The compound of claim 1, wherein the compound is selected from:
(6aR,10aR)-6,6a,7,8,9,10,10a,11-octahydro-1,3-dioxa-7-aza-cyclopenta[a]anthracene
(6aR,10aR)-7-methyl-6,6a,7,8,9,10,10a,11-octahydro-1,3-dioxa-7-azacyclopenta[a]anthracene
(6aR,10aR)-7-ethyl-6,6a,7,8,9,10,10a,11-octahydro-1,3-dioxa-7-aza-cyclopenta[a]anthracene
(6aR,10aR)-7-n-propyl-6,6a,7,8,9,10,10a,11-octahydro-1,3-dioxa-7-aza-cyclopenta[a]anthracene
or a pharmaceutically acceptable acid addition salt thereof.

8. The compound according to claim 6 wherein $R_1$ and $R_2$ are fused and form a methylene ($CH_2$) group, and $R_3$ is selected from the group consisting of hydrogen, methyl, ethyl and n-propyl.

9. A pharmaceutical composition comprising a therapeutically effective amount of a compound of formula I and one or more pharmaceutically acceptable carriers, diluents and excipients, the compound of formula I having the following structure:

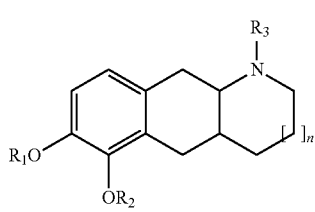

wherein n=1
wherein $R_1$ and $R_2$ are fused and form a methylene ($CH_2$) group, a carbonyl (C=O) group, or an oxalyl (O=C—C=O) group
$R_3$ is selected from the group consisting of hydrogen, methyl, ethyl, n-propyl, cyclo-propyl, cyclo-butyl, allyl, propargyl and hydroxyethyl,
and pharmaceutically acceptable acid addition salts thereof.

10. A pharmaceutical composition according to claim 9, wherein $R_1$ and $R_2$ are fused and form a methylene ($CH_2$) group, and $R_3$ is selected from the group consisting of hydrogen, methyl, ethyl and n-propyl, for non-oral administration.

11. A pharmaceutical composition according to claim 10 for transdermal, nasal, buccal, intramuscular, parenteral, or subcutaneous administration.

12. A pharmaceutical composition according to claim 9, wherein the compound of formula I is a substantially pure diastereoisomer or a substantially pure enantiomer.

* * * * *